United States Patent [19]

Kraus et al.

[11] Patent Number: 5,916,755

[45] Date of Patent: Jun. 29, 1999

[54] METHODS OF CHARACTERIZING LIGANDS FOR THE ERBB-3 RECEPTOR, METHODS OF INFLUENCING ERBB-3 ACTIVITIES AND METHODS OF DIAGNOSING ERBB-3-RELATED NEOPLASM

[75] Inventors: Matthias H. Kraus, Bethesda, Md.; Stuart A. Aaronson, Vienna, Va.

[73] Assignee: The United States of America as represented by the Department of Health and Human Services, Washington, D.C.

[21] Appl. No.: 08/475,352

[22] Filed: Jun. 7, 1995

Related U.S. Application Data

[60] Division of application No. 07/978,895, Nov. 10, 1992, Pat. No. 5,480,968, which is a continuation-in-part of application No. 07/444,406, Dec. 1, 1989, Pat. No. 5,183,884.

[51] Int. Cl.$^6$ ...................... G01N 33/566; G01N 33/536; C07K 14/71; G12Q 1/68

[52] U.S. Cl. ........................... 435/7.1; 435/7.2; 435/325; 435/6; 435/7.21; 436/501; 530/350; 530/399; 530/387.7; 530/388.22

[58] Field of Search .................................... 530/350, 399, 530/387.7, 388.22; 435/325, 6, 7.2, 7.21, 7.1; 436/501

[56] References Cited

U.S. PATENT DOCUMENTS

| | | |
|---|---|---|
| 4,867,973 | 9/1989 | Goers et al. . |
| 5,183,884 | 2/1993 | Kraus et al. ............................ 536/23.5 |
| 5,480,968 | 1/1996 | Kraus et al. ............................ 530/326 |

FOREIGN PATENT DOCUMENTS

| | | |
|---|---|---|
| 0444961 | 4/1991 | European Pat. Off. . |

OTHER PUBLICATIONS

Pearson and Lipman, Proc. Natl. Acad. Sci. USA 85:2444–2448, 1988.
Pierce et al., Science 239:628–631, 1988.
Kraus et al., EMBO Journal 6:605–610, 1987.
Plowman et al., Proc. Natl. Acad. Sci. USA 87:4905–4909, 1990.
Kraus et al., Proc. Natl. Acad. Sci. USA 86:9193–9197, 1989.
King et al., Science 229:974–978, 1985.
Semba et al., Proc. Natl. Acad. Sci. USA 82:6497–6501, 1985.
Coussens et al., Science 230:1132–1139, 1985.
Yamamoto et al., Nature 319:230–234, 1986.
Di Fiore et al., Science 237:178–182, 1987.
Drebin et al., Proc. Natl. Acad. Sci. USA 83:9129–9133 (1986).

(List continued on next page.)

*Primary Examiner*—Stephen Walsh
*Assistant Examiner*—Claire M. Kaufman

[57] ABSTRACT

A DNA fragment distinct from the epidermal growth factor receptor (EGFR) and erbB-2 genes was detected by reduced stringency hybridization of v-erbB to normal genomic human DNA. cDNA cloning revealed a predicted 148 kd transmembrane polypeptide with structural features identifying it as a member of the erbB family, prompting designation of the new gene as erbB-3. It was shown to be expressed as a 6.2 kb transcript in a variety of normal tissues of epithelial origin. Markedly elevated erbB-3 mRNA levels were demonstrated in certain human mammary tumor cell lines. These findings indicate that increased erbB-3 expression, as in the case of EGFR and erbB-2, plays a role in some human malignancies. Using erbB-3 specific antibodies (polyclonal or monoclonal), the erbB-3 protein was identified as a 180 kDa glycoprotein, gp180$^{erbB-3}$. The intrinsic catalytic function of gp180$^{erbB-3}$ was uncovered by its ability to autophosphorylate in vitro. These findings, combined with the detection of constitutive tyrosine phosphorylation of gp180$^{erbB-3}$ in 4 out of 12 human mammary tumor cell lines, implicate the activated erbB-3 product in the pathogenesis of some human malignancies. Thus, this invention also relates to a method for detecting a receptor ligand capable of either activating or down-regulating the receptor protein, as well as procedures for purifying the resultant ligand; and a method of screening potential ligand analogs for their ability to activate the receptor protein.

31 Claims, 14 Drawing Sheets

U.S. PATENT DOCUMENTS

Kraus et al., UCLA Symposia on Molecular & Cellular Biology, 19th Annual Meetings, Abstract F226 (1990).

Carpenter et al., Receptors for the epidermal growth factor and other polypeptide mitogens, Ann. Rev. Biochem., 56:881–914, 1987.

FIGURE 3 (SEQ ID NO:1)

```
GAATTCCAGA TCTCAGTGAC TGATTCCCCC AACCTTAAGA ATACTTTCTT CCCCTATACC    60

TACAG GGA ATG TAC TAC CTT GAG GAA CAT GGT ATG GTG CAT AGA AAC       107
      Gly Met Tyr Tyr Leu Glu Glu His Gly Met Val His Arg Asn

CTG GCT GCC CGA AAC GTG CTA CTC AAG TCA CCC AGT CAG GTT CAG GTG     155
Leu Ala Ala Arg Asn Val Leu Leu Lys Ser Pro Ser Gln Val Gln Val

GCA GAT TTT GGT GTG GCT GAC CTG CTG CCT CCT GAT GAT AAG CAG CTG     203
Ala Asp Phe Gly Val Ala Asp Leu Leu Pro Pro Asp Asp Lys Gln Leu

CTA TAC AGT GAG GCC AAG GTGAGGAGAC ACAAAGGGTA AGGAGGCGGG            251
Leu Tyr Ser Glu Ala Lys

GGTGGAGTGA AGCATGGGGA TAGGGAGCAG CCAGTGGTCT CTTCCAGAGG CAAGCAGATG   311
CTTCATGGTA AGTTCAAGGA GAGAAGGCTG CAGATGCCAG ATATTTTAGT TCAGAGGGCA   371
ACAAAGAAAA TAATGATCAA GAACTTGGGA CTGGCCGGGC GCGGTGGCTC ACGCCTGTAA   431
TCCCAACACT TCGGGAGGCC AAGGCGGGTG GATCACAAGG TCAGGAGATC AAGACCATCC   491
TGGCTAGCAC GGTGAAACCC CGTCTCTACT AAATATACAA AAAAAAAAAA ATTAGCCAGG   551
CGTGGCGGCA TGCATCTGTA CTCCCAGCTA CTCGGGAGGC TGAGGCAGGA GAATGGCGTG   611
AACCCAGGAG GCGGAGCTTG CAGTGGGCCG AGATCGCACC ACTGCACTCC AGTCTGGGCG   671
ACAGAGCGAG ACTCCGTCTC AAAAAAAAAA AAAAAAGAAT TTGGGACTTG GAAATCCTAA   731
GAAAATTTGT GGAAATAAAC TTGTGATACC TCTATCTTTA ATCCGCAG ACT CCA ATT    788
                                                    Thr Pro Ile

AAG TGG ATG GCC CTT GAG AGT ATC CAC TTT GGG AAA TAC ACA CAC CAG     836
Lys Trp Met Ala Leu Glu Ser Ile His Phe Gly Lys Tyr Thr His Gln

AGT GAT GTC TGG AGC TAT  G GTCAGTGCAT CTGGATGCCC TCTCTACCAT         885
Ser Asp Val Trp Ser Tyr

CACTGGCCCC AGTTTCAAAT TTACCTTTTG AGAGCCCCCT CTTAGAATCT CTAAGCACTT   945
CAGATTTTTG TGTTAGATCA GGTTCTGCCT TCCCTTCACT TCATGCCCAT GTCTACTATT  1005
TTGCCAGTGA CTAGTCCATG TCTTCCTGCA ACAG  GT GTG ACA GTT TGG GAG      1056
                                      Gly Val Thr Val Trp Glu

TTG ATG ACC TTC GGG GCA GAG CCC TAT GCA GGG CTA CGA TTG GCT GAA    1104
Leu Met Thr Phe Gly Ala Glu Pro Tyr Ala Gly Leu Arg Leu Ala Glu

GTA CCA GAC CTG CTA GAG AAG GGG GAG CGG TTG GCA CAG CCC CAG ATC    1152
Val Pro Asp Leu Leu Glu Lys Gly Glu Arg Leu Ala Gln Pro Gln Ile

TGC ACA ATT GAT GTC TAC ATG GTG ATG GTC AAG TGTGAGTTAC CTGCTGAGCC 1205
Cys Thr Ile Asp Val Tyr Met Val Met Val Lys

CAACCATTTT CTCTTTTTTT CTTTTTTTTT CTTTTTTTTT TTTTTTTGAG ACAGAGTCTC  1265
ACAATTGTCA CCCAGGCTGG AGTGCAATGG TGCAATCAAT CTTGGCTCAC TACAACCTCC  1325
GCCTCTCGGG TTCAAGAGAT TCTCCTGCTT CAGCTCCGGA GTAGCTGGGA TTACAGCGCC  1385
CGCCACACCT GGATAACTGT TACACTTTTA GTAGAGATGG GGTTTCACCA TGTTGGCCAG  1445
GCTGGTCTCA AACTCCTGAC CTCAGGTGAT CCGCCTGCCT CAGCTTCCCA AAGTGCTGGG  1505
ATTACAGGTG TGAGCCATCA TGCTCGCCTG ACTGCAG                          1542
```

| | | | | | | |
|---|---|---|---|---|---|---|
| MRANDALQVL | GLLFSLARGS | EVGNSQAVCP | GTLNGLSVTG | DAENQYQTLY | KLYERCEVVM | GNLEIVLTGH | 70 |

NADLSFLQWI REVTGYVLVA MNEFSTLPLP NLRVVRGTQV YDGKFAIFVM LNYNTNSSHA LRQLRLTQLT 140

EILSGGVYIE KNDKLCHMDT IDWRDIVRDR DAEIVVKDNG RSCPPCHEVC KGRCWGPGSE DCQTLTKTIC 210

APQCNGHCFG PNPNQCCHDE CAGGCSGPQD TDCFACRHFN DSGACVPRCP QPLVYNKLTF QLEPNPHTKY 280

QYGGVCVASC PHNFVVDQTS CVRACPPDKM EVDKNGLKMC EPCGGLCPKA CEGTGSGSRF QTVDSSNIDG 350

FVNCTKILGN LDFLITGLNG DPWHKIPALD PEKLNVFRTV REITGYLNIQ SWPPHMHNFS VFSNLTTIGG 420

RSLYNRGFSL LIMKNLNVTS LGFRSLKEIS AGRIYISANR QLCYHHSLNW TKVLRGPTEE RLDIKHNRPR 490

RDCVAEGKVC DPLCSSGGCW GPGPGQCLSC RNYSRGGVCV THCNFLNGEP REFAHEAECF SCHPECQPME 560

GTATCNGSGS DTCAQCAHFR DGPHCVSSCP HGVLGAKGPI YKYPDVQNEC RPCHENCTQG CKGPELQDCL 630

GQTLVLIGKT HLTMALTVIA GLVVIFMMLG GTFLYWRGRR IQNKRAMRRY LERGESIEPL DPSEKANKVL 700

ARIFKETELR KLKVLGSGVF GTVHKGVWIP EGESIKIPVC IKVIEDKSGR QSFQAVTDHM LAIGSLDHAH 770

IVRLLGLCPG SSLQLVTQYL PLGSLLDHVR QHRGALGPQL LLNWGVQIAK GMYYLEEHGM VHRNLAARNV 840

LLKSPSQVQV ADFGVADLLP PDDKQLLYSE AKTPIKWMAL ESIHFGKYTH QSDVWSYGVT VWELMTFGAE 910

PYAGLRLAEV PDLLEKGERL AQPQICTIDV YMVMVKCWMI DENIRPTFKE LANEFTRMAR DPPRYLVIKR 980

ESGPGIAPGP EPHGLTNKKL EEVELEPELD LDLDLEAEED NLATTTLGSA LSLPVGTLNR PRGSQSLLSP 1050

SSGYMPMNQG NLGESCQESA VSGSSERCPR PVSLHPMPRG CLASESSEGH VTGSEAELQE KVSMCRSRSR 1120

SRSPRPRGDS AYHSQRHSLL TPVTPLSPPG LEEEDVNGYV MPDTHLKGTP SSREGTLSSV GLSSVLGTEE 1190

EDEDEEYEYM NRRRRHSPPH PPRPSSLEEL GYEYMDVGSD LSASLGSTQS CPLHPVPIMP TAGTTPDEDY 1260

EYMNRQRDGG GPGGDYAAMG ACPASEQGYE EMRAFQGPGH QAPHVHYARL KTLRSLEATD SAFDNPDYWH 1330

SRLFPKANAQ RT 1342

FIG.4A (SEQ ID NO:4)

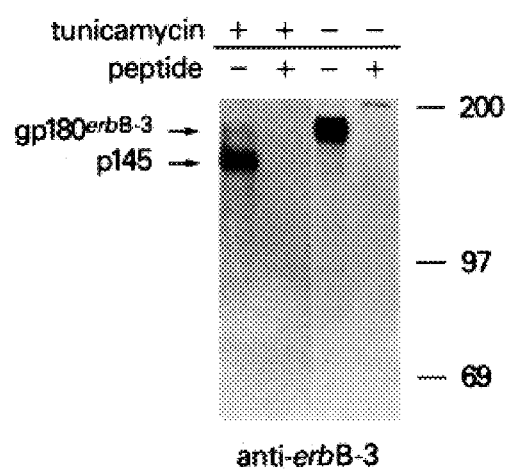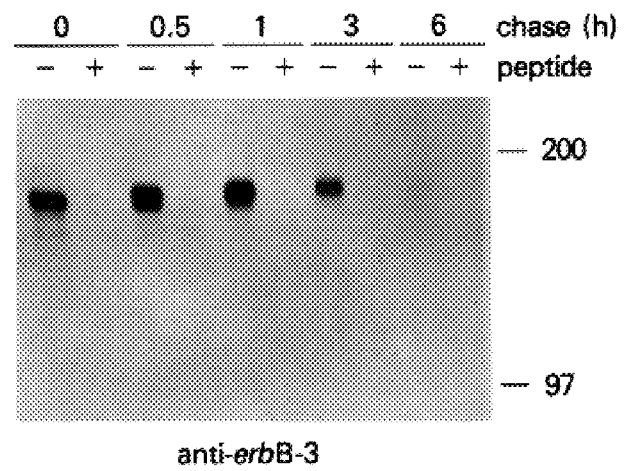
FIG.8B                    FIG.8C

METHODS OF CHARACTERIZING LIGANDS FOR THE ERBB-3 RECEPTOR, METHODS OF INFLUENCING ERBB-3 ACTIVITIES AND METHODS OF DIAGNOSING ERBB-3-RELATED NEOPLASM

This application is a Divisional application of Ser. No. 07/978,895, filed Nov. 10, 1992, now U.S. Pat. No. 5,480,968 issued Jan. 2, 1996 which is a continuation-in-part of Ser. No. 07/444,406, filed Dec. 1, 1989, now U.S. Pat. No. 5,183,884 issued Feb. 2, 1993.

FIELD OF THE INVENTION

The present invention relates to genes which encode novel proteins related to a family of receptor proteins typified by two related membrane spanning tyrosine kinases: the Epidermal Growth Factor receptor (EGFR), which is encoded by the erbB gene, the normal human counterpart of an oncogene (v-erbB) that was first recognized in the proviral DNA of avian erythroblastosis virus; and the receptor encoded by the related gene erbB-2. In particular, the present invention relates to a DNA segment encoding the coding sequence, or a unique portion thereof, for a third member of this receptor gene family, herein designated erbB-3.

BACKGROUND OF THE INVENTION

Proto-oncogenes encoding growth factor receptors constitute several distinct families with close overall structural homology. The highest degree of homology is observed in their catalytic domains, essential for the intrinsic tyrosine kinase activity of these proteins. Examples of such receptor families include: the EGFR and the related product of the erbB-2 oncogene; the Colony Stimulating Factor 1 receptor (CSF-1-R) and the related Platelet-Derived Growth Factor receptor (PDGF-R); the insulin receptor (IR) and the related Insulin-like Growth factor 1 receptor (IGF-1R); and the receptors encoded by the related oncogenes eph and elk.

It is well established that growth factor receptors in several of these families play critical roles in regulation of normal growth and development. Recent studies in Drosophila have emphasized how critical and multifunctional are developmental processes mediated by ligand-receptor interactions. An increasing number of Drosophila mutants with often varying phenotypes have now been identified as being due to lesions in genes encoding such proteins. The genetic locus of the Drosophila EGFR homologue, designated DER, has recently been identified as being allelic to the zygotic embryonic lethal faint little ball exhibiting a complex phenotype with deterioration of multiple tissue components of ectodermal origin. Furthermore, other mutants appear to lack DER function either in the egg or the surrounding maternal tissue. Thus, the DER receptor may play an important role in the ligand-receptor interaction between egg and follicle cells necessary for determination of correct shape of eggshell and embryo. It is not yet known whether DER represents the sole Drosophila counterpart of known mammalian erbB-related genes.

Some of these receptor molecules have been implicated in the neoplastic process as well. In particular, both the erbB and erbB-2 genes have been shown to be activated as oncogenes by mechanisms involving overexpression or mutations that constitutively activate the catalytic activity of their encoded receptor proteins (Bargmann, C. I., Hung, M. C. & Weinberg, R. A., 1986, Cell 45:649–657; Di Fiore, P. P., Pierce, J. H., Kraus, M. H., Segatto, O., King, C. R. & Aaronson, S. A., 1987, Science 237:178–182; Di Fiore, P. P., Pierce, J. H., Fleming, T. P., Hazan, R., Ullrich, A., King, C. R., Schlessinger, J. & Aaronson, S. A., 1987, Cell 51:1063–1070; Velu, T. J., Beguinot, L., Vass, W. C., Willingham, M. C., Merlino, G. T., Pastan, I. & Lowy, D. R., 1987, Science 238:1408–1410). Both erbB and erbB-2 have been causally implicated in human malignancy. erbB gene amplification or overexpression, or a combination of both, has been demonstrated in squamous cell carcinomas and glioblastomas (Libermann, T. A., Nusbaum, H. R., Razon, N., Kris, R., Lax, I., Soreq, H., Whittle, N., Waterfield, M. D., Ullrich, A. & Schlessinger, J., 1985, Nature 313:144–147). erbB-2 amplification and overexpression have been observed in human breast and ovarian carcinomas (King, C. R., Kraus, M. H. & Aaronson, S. A., 1985, Science 229:974–976; Slamon, D. J., Godolphin, W., Jones, L. A., Holt, J. A., Wong, S. G., Keith, D. E., Levin, W. J., Stuart, S. G., Udove, J., Ullrich, A. & Press, M. F., 1989, Science 244:707–712), and erbB-2 overexpression has been reported to be an important prognostic indicator of particularly aggressive tumors (Slamon, D. J., et al., 1989, supra). Yet, not all such tumors have been found to overexpress erbB-2, and many human tumors have not yet been associated with any known oncogene. Thus, there has been a continuing need to search for additional oncogenes which would provide knowledge and methods for diagnosis and, ultimately, for rational molecular therapy of human cancers.

Throughout this application, various publications are referenced. The disclosures of these publications in their entireties are hereby incorporated by reference into this application in order to more fully describe the state of the art to which this invention pertains.

SUMMARY OF THE INVENTION

It is an object of present invention to provide a DNA segment encoding a receptor protein related to the erbB proto-oncogene family which previously has not been known or even suspected to exist. Further, it is an object of the present invention to develop assays for expression of the RNA and protein products of such genes to enable determining whether abnormal expression of such genes is involved in human cancers. Thus, further objects of this invention include providing antibodies, either polyclonal or monoclonal, specific to a unique portion of the receptor protein; a method for detecting the presence of an erbB-3 ligand that is capable of either activating or down-regulating the receptor protein as well as procedures for purifying the resultant ligand; a method of screening potential ligand analogs for their ability to activate the receptor protein; and procedures for targeting a therapeutic drug to cells having a high level of the receptor protein.

In pursuit of the above objects, the present inventors have discovered a human genomic DNA fragment that is produced by cleavage with the SacI restriction enzyme, has a size of about 9 kbp, and is detectable by nucleic acid hybridization with a probe derived from the v-erbB gene only under reduced stringency hybridization conditions. Thus, this DNA fragment is distinct from those known to encode the epidermal growth factor receptor (EGFR) (i.e., the erbB gene) and from the related erbB-2 gene. Characterization of this DNA fragment after partial purification and molecular cloning showed that the region of v-erbB homology mapped to three exons that encode amino acid sequences having homologies of 64% and 67% to contiguous regions within the tyrosine kinase domains of the EGFR and erbB-2 proteins, respectively. A probe derived from the genomic DNA clone identified cDNA clones of the related mRNA which encode a predicted 148 kDa transmembrane polypeptide with structural features identifying it as a member of the erbB family, prompting designation of the new gene as erbB-3. This gene was mapped to human chromosome 12q11–13 and was shown to be expressed as a 6.2 kb transcript in a variety of normal tissues of epithelial origin. Markedly elevated erbB-3 mRNA levels were demonstrated in certain human mammary tumor cell lines.

The predicted human erbB-3 gene product is closely related to EGFR and erbB-2, which have been implicated as oncogenes in model systems and human neoplasia. The erbB-3 coding sequence was expressed in NIH/3T3 fibroblasts and its product was identified as a 180 kDa glycoprotein, $gp180^{erbB-3}$. Tunicamycin and pulse-chase experiments revealed that the mature protein was processed by N-linked glycosylation of a 145 kDa erbB-3 core polypeptide. The intrinsic catalytic function of $gp180^{erbB-3}$ was uncovered by its ability to autophosphorylate in vitro. Ligand-dependent signaling of its cytoplasmic domain was established employing transfectants which express a chimeric EGFR/erbB-3 protein, $gp180^{EGFR/erbB-3}$. EGF induced tyrosine phosphorylation of the chimera and promoted soft agar colony formation of such transfectants. These findings, combined with the detection of constitutive tyrosine phosphorylation of $gp180^{erbB-3}$ in 4 out of 12 human mammary tumor cell lines, implicates the activated erbB-3 product in the pathogenesis of some human malignancies.

Accordingly, in a principal embodiment, the present invention relates to a DNA segment having a nucleotide sequence that encodes an erbB-3 gene or a unique portion thereof. This portion of an erbB-3 gene includes at least about 12 to 14 nucleotides which are sufficient to allow formation of a stable duplex with a DNA or RNA segment having sequences complementary to those in this portion of an erbB-3 gene. Further, this unique portion of an erbB-3 gene, of course, has a sequence not present in an erbB or an erbB-2 gene. In other words, the sequence of this portion of an erbB-3 gene differs in at least one nucleotide from the sequence of any other DNA segment. In one embodiment, this DNA segment is exemplified by a human genomic DNA fragment that is produced by cleavage with the SacI restriction enzyme, has a size of about 9 kbp, and is detectable by nucleic acid hybridization with a probe derived from the v-erbB gene only under reduced stringency hybridization conditions, as described in Example 1. By application of the nucleic acid hybridization and cloning methods described in the present disclosure, without undue experimentation, one of ordinary skill in the art of recombinant DNA is enabled to identify and isolate DNA fragments related to the present human DNA fragment comprising a nucleotide sequence that encodes at least a portion of a mammalian erbB-3 gene other than the human erbB-3 gene. Application of the genomic DNA fragment of the erbB-3 gene as a probe in hybridization methods also enables one of ordinary skill in the art to obtain an entire erbB-3 gene, by sequential isolation of overlapping fragments adjoining the present fragment, i.e., by an approach known in the art as chromosome walking.

The present disclosure describes the partial nucleotide sequence of the human genomic 9 kbp SacI DNA fragment, within the region of homology to the v-erbB gene; however, the methods in the present disclosure further enable the isolation and determination of the sequence of the entire 9 kbp human genomic DNA fragment according to the present invention. Accordingly, the present invention further relates to a DNA segment having the nucleotide sequence, or a unique portion thereof, of a human genomic DNA fragment that is produced by cleavage with the SacI restriction enzyme, has a size of about 9 kbp, and is detectable by nucleic acid hybridization with a probe derived from the v-erbB gene only under reduced stringency hybridization conditions, as described in Example 1. By extension of the chromosome walking approach noted above, the present invention further enables one of ordinary skill in the art to determine the sequences of related DNA fragments comprising the complete human erbB-3 gene as well as erbB-3 genes of, for example, mammals other than human.

In the application of the present SacI DNA fragment or any portion thereof as a probe for nucleic acid hybridization, the fragment is amplified, for example, by the in vitro polymerase chain reaction method (PCR; see U.S. Pat. No. 4,683,202; U.S. Pat. No. 4,683,195; and Saiki et al., 1985, *Science* 230:1350–54) or by standard methods of molecular cloning. For example, a clone of the human erbB-3 gene DNA segment according to the present invention is exemplified by a recombinant clone of a normal human thymus DNA fragment, herein designated as the E3-1 genomic clone, having the partial restriction enzyme map defined in FIG. 2 and the partial DNA sequence defined in FIG. 3 and SEQ ID NO:1 of the present application. Isolation and characterization of genomic clone E3-1 is described in Example 2, below.

Analysis of the nucleotide sequences of the human genomic DNA segment according to the present invention reveals that the nucleotide sequence encodes three open reading frames bordered by splice junction consensus sequences which define the boundaries between nontranslated intron sequences and the translated exons (shown in FIG. 2 and SEQ ID NO:1). The predicted amino acid sequences of the three exons (SEQ ID NOS:1 and 2) are highly similar to three regions which are contiguous in the tyrosine kinase domains of v-erbB, as well as human EGFR and erbB-2 proteins. Moreover, the predicted amino acid sequences of this human genomic clone are included in a larger open reading frame in complementary DNA (cDNA) clones of an mRNA species that is detected by hybridization of a probe derived from the human genomic DNA clone.

Accordingly, the present invention also relates to a DNA segment having a nucleotide sequence of an erbB-3 gene in which that nucleotide sequence encodes the amino acid sequence of an erbB-3 protein or a unique portion thereof. In other words, the sequence of this portion of an erbB-3 amino acid sequence differs in at least one amino acid residue from the amino acid sequence encoded by any other DNA segment. This portion of an erbB-3 amino acid sequence includes at least about 4 to 6 amino acids which are sufficient to provide a binding site for an antibody specific for this portion of the erbB-3 polypeptide. Further, this unique portion of an erbB-3 amino acid sequence, of course, includes sequences not present in an erbB or an erbB-2 gene. In particular, the present invention relates to such a DNA segment for which this amino acid sequence or unique portion thereof is that of the polypeptide product of the human erbB-3 gene. This DNA segment is exemplified by the human genomic DNA clone E3-1, above, as well as by human cDNA clones designated E3-6, E3-8, E3-9, E3-11 and E3-16, which are described in Example 3 below. A preferred embodiment of this DNA segment that encodes the amino acid sequence of the entire polypeptide product of the human erbB-3 gene is human cDNA clone E3-16 having the nucleotide sequence defined in SEQ ID NO:3 and having the predicted amino acid sequence defined in SEQ ID NOS:3 and 4.

The DNA segments according to this invention are useful for detection of expression of erbB-3 genes in normal and tumor tissues, as described in Example 5 below. Therefore, in yet another aspect, the present invention relates to a bioassay for determining the amount of erbB-3 mRNA in a biological sample comprising the steps of: i) contacting that biological sample with a nucleic acid isolate consisting essentially of a nucleotide sequence that encodes erbB-3 or a unique portion thereof under conditions such that a nucleic acid:RNA hybrid molecule, such as a DNA:RNA hybrid molecule, can be formed; and ii) determining the amount of hybrid molecule present, the amount of hybrid molecule indicating the amount of erbB-3 mRNA in the sample. Findings described in Example 5, below, indicate that increased erbB-3 expression, as detected by this method of this invention, plays a role in some human malignancies, as is the case for the EGFR (erbB) and erbB-2 genes.

Of course, it will be understood by one skilled in the art of genetic engineering that in relation to production of erbB-3 polypeptide products, the, present invention also includes DNA segments having DNA sequences other than those in the present examples that also encode the amino acid sequence of the polypeptide product of an erbB-3 gene. For example, it is known that by reference to the universal genetic code, standard genetic engineering methods can be used to produce synthetic DNA segments having various sequences that encode any given amino acid sequence. Such synthetic DNA segments encoding at least a portion of the amino acid sequence of the polypeptide product of the human erbB-3 gene also fall within the scope of the present invention. Further, it is known that different individuals may have slightly different DNA sequences for any given human gene and, in some cases, such mutant or variant genes encode polypeptide products having amino acid sequences which differ among individuals without affecting the essential function of the polypeptide product. Still further, it is also known that many amino acid substitutions can be made in a polypeptide product by genetic engineering methods without affecting the essential function of that polypeptide. Accordingly, the present invention further relates to a DNA segment having a nucleotide sequence that encodes an amino acid sequence differing in at least one amino acid from the amino acid sequence of human erbB-3, or a unique portion thereof, and having greater overall similarity to the amino acid sequence of human erbB-3 than to that of any other polypeptide. The amino acid sequence of this DNA segment includes at least about 4 to 6 amino acids which are sufficient to provide a binding site for an antibody specific for the portion of a polypeptide containing this sequence. In a preferred embodiment, this DNA segment encodes an amino acid sequence having substantially the function of the human erbB-3 polypeptide. As noted above, the predicted erbB-3 polypeptide is a 148 kDa transmembrane polypeptide with structural features identifying it as a member of the erbB receptor family.

The similarity of the amino acid sequence of the present invention with that of an erbB-3 amino acid sequence is determined by the method of analysis defined by the sequence alignment and comparison algorithms described by Pearson and Lipman (Pearson, W. R. & Lipman, D. J., 1988, *Proc. Nat. Acad. Sci. U.S.A.* 85:2444–48). This comparison contemplates not only precise homology of amino acid sequences, but also substitutions of one residue for another which are known to occur frequently in families of evolutionarily related proteins sharing a conserved function.

The present invention further relates to a recombinant DNA molecule comprising a DNA segment of this invention and a vector. In yet another aspect, the present invention relates to a culture of cells transformed with a DNA segment according to this invention. These host cells transformed with DNAs of the invention include both higher eukaryotes, including animal, plant and insect cells, and lower eukaryotes, such as yeast cells, as well as prokaryotic hosts including bacterial cells such as those of *E. coli* and *Bacillus subtilis*. These aspects of the invention are exemplified by recombinant DNAs and cells described in Examples 2, 3 and 6, below.

One particular embodiment of this aspect of this invention comprises a cell, preferably a mammalian cell, transformed with a DNA of the invention, wherein the transforming DNA is capable of being expressed to produce the functional polypeptide of an erbB-3 gene. For example, mammalian cells (COS-1) transformed with the pSV2 gpt vector carrying the E3-16 cDNA are prepared according to well-known methods (such as those described in U.S. patent application Ser. No. 07/308,302 of Matsui et al., filed Feb. 9, 1989; see also Pierce, J. H. et al., 1988, *Science* 239:628–631; and Matsui, T., Heidaran, M., Miki, T., Popescu, N., La Rochelle, W., Kraus, M., Pierce, J. & Aaronson, S., 1989 *Science* 243:800–804). Briefly, cDNA expression plasmids are constructed by introducing the erbB-3-related cDNA encompassing all the nucleotides in the open reading frame into the pSV2 gpt vector into which the simian sarcoma virus long-terminal-repeat (LTR) had been engineered as the promoter, as previously described in detail. Transient expression of the erbB-3 gene in such recombinant vectors is achieved by transfection into COS-1 cells.

Stable expression of an erbB-3 gene can also be obtained with mammalian expression vectors such as the pZIP-NEOSVX vector (Cepko, C. L., Roberts B. E. and Mulligan, R. C., 1984, *Cell* 37:1053–62). For example, a eukaryotic expression vector was engineered by cloning the full-length erbB-3 coding sequence derived from cDNA clone E3-16 into the BamHI site of the pZIPNEOSVX vector DNA adapting the DNA fragments with synthetic oligonucleotides. NIH/3T3 cells were transfected with 1 μg of recombinant expression vector DNA (LTR-erbB-3) and selected with the resistance marker antibiotic G418. To detect expression of erbB-3, polyclonal rabbit antiserum was raised against a synthetic peptide (such as amino acid (aa) positions 1191–1205 (SEQ ID NO:5); aa 1254–1268 (SEQ ID NO:6); aa 478–492 (SEQ ID NO:7); aa 1116–1330 (SEQ ID NO:8) and aa 1199–1213 (SEQ ID NO:9)). These peptide epitopes are located intracellularly within the predicted carboxyl terminus of the erbB-3 coding sequence with the exception of aa 478–492, which resides in the extracellular domain of the erbB-3 protein. For example, as shown in FIG. 7, immunoblotting analysis using antiserum raised against aa 1191–1205 led to detection of the erbB-3 protein (FIG. 7A). The specificity of erbB-3 protein detection was demonstrated by preincubating the antiserum with the homologous peptide (FIG. 7B). Moreover, the normal 180 kDa erbB-3 protein was specifically detected with the polyclonal antiserum only in cells transfected with the recombinant erbB-3 expression vector, while control NIH3T3 cells that were not transfected with the vector were negative. There was no cross-reactivity of the above-listed antisera with the related EGFR or erbB-2 proteins overexpressed in NIH/3T3 cells. The stably transfected NIH3T3 cells are useful as erbB-3 receptor protein sources for testing potential candidates for an erbB-3-specific ligand, analysis of the biological activity, as well as generation of monoclonal antibodies raised against the native erbB-3 protein. An erbB-3-specific ligand is identified by detection of autophosphorylation of the erbB-3 receptor protein, stimulation of DNA synthesis or induction of the transformed phenotype of the LTR-erbB-3 transfected NIH3T3 cells.

Alternatively, other transformed cell systems are available for functional expression of receptors of the erbB receptor family, for example, a system based on the 32D cell line, a mouse hematopoietic cell line normally dependent on interleukin-3 (I6-3) for survival and proliferation. Recent studies have established that introduction of an expression vector for the EGFR in these cells leads to effective coupling with EGF mitogenic signal transduction pathways, thereby allowing a ligand of the EGFR to replace I6-3 in supporting survival and growth of the 32D cells. By employing the known methods described for the EGFR, for example (Pierce, J. H. et al., 1988, supra), the E3-16 cDNA of the present invention is expressed to produce functional receptors in 32D cells which are then useful for examining the biological function of these erbB-3 receptors, for instance, the specificity of their ligand binding capacity and coupling capacities to secondary messenger systems. Thus, by so using gene expression methods described herein with the DNAs of the present invention, especially the preferred E3-16 cDNA clone, one of ordinary skill in the art, without undue experimentation, can construct cell systems which fall within the scope of this invention, for determining the mechanisms of erbB-3 regulatory processes. Accordingly, the present invention also relates to a bioassay for screening potential analogs of ligands of erbB-3 receptors for the ability to affect an activity mediated by erbB-3 receptors, comprising the steps of: i) contacting a molecule suspected of being a ligand with erbB-3 receptors produced by a cell that yields functional erbB-3 receptors; ii) determining the amount of a biological activity mediated by those erbB-3 receptors; and iii) selecting those analogs which affect the biological activity mediated by the erbB-3 receptors. For example, a compound can be added to a cell having normal or low level erbB-3 phosphorylation. The amount of erbB-3 phosphorylation is then measured and compared to the level prior to adding the compound. The presence of increased activity can then be selected. Alternatively, a cell with high or constitutive erbB-3 phosphorylation can be used to screen for compounds which decrease activity. In addition, an erbB-3 ligand or analogs can be used in this system to screen for the amount of ligand which is necessary to promote or inhibit phosphorylation.

Various standard recombinant systems, such as those cited above as well as others known in the art, are suitable as well for production of large amounts of the novel erbB-3 receptor protein using methods of isolation for receptor proteins that are well known in the art. Therefore, the present invention also encompasses an isolated polypeptide having at least a portion of the amino acid sequence defined in FIG. 4 (SEQ ID NO:4), such as those polypeptides given by SEQ ID NOS:5–9.

The invention further presents results undertaken in an effort to identify and characterize the normal erbB-3 gene product (Examples 6–8). By analysis of an EGFR/erbB-3 chimeric receptor, this invention demonstrates that EGF dependent activation of the erbB-3 catalytic domain results in a proliferative response in transfected NIH/3T3 cells. Further, the invention shows that some human mammary tumor cell lines exhibit a dramatic elevation of steady state erbB-3 tyrosine phosphorylation, implying functional erbB-3 activation in these tumor cells.

The identification of erbB-3 ligands is of great importance because, for instance, the availability of these ligands will facilitate the complete characterization of erbB-3 biological function as well as development of therapeutic strategies involving the ligands. In particular, the instant observation of functional erbB-3 activation in mammary tumor cells at steady state raises the possibility that a role of erbB-3 in human tumors involves autocrine activation. That is, the simultaneous expression of the ligand by the tumor cell may constitutively activate erbB-3, leading to an uncontrolled proliferative growth response. Accordingly, this invention provides for the detection, purification and characterization of erbB-3 ligands, particularly erbB-3 ligands that are capable of either activating or down-regulating (blocking the activation of) the erbB-3 protein.

The ligand detection and purification method of this invention capitalizes on the erbB-3 expression and activation characteristics in certain cell lines as well as the common property of growth factor receptor tyrosine kinases to rapidly autophosphorylate on tyrosine residues in response to ligand triggering to detect activating or blocking ligand from source containing potential erbB-3 ligands, as described in Example 9. Therefore, in yet another aspect, the present invention relates to a method for detecting the presence of an erbB-3 ligand in a source containing a potential erbB-3 ligand, comprising the steps of a) contacting a first sample of cells from a cell line that expresses erbB-3 protein with the source containing a potential erbB-3 ligand for a time and under conditions sufficient to allow erbB-3 ligand contained in the source to bind to erbB-3 protein to form a triggered sample, wherein the cell line expresses erbB-3 protein having low level intrinsic tyrosine phosphorylation; b) contacting a second sample of cells from the cell line with a control medium (unconditioned serum free medium) for the time and under the conditions as given in step a) above to form a control sample; c) determining the level of erbB-3 activation in the triggered sample and in the control sample; and d) comparing the level of erbB-3 activation in the triggered sample with the level of erbB-3 activation in the control sample, wherein an increase in activation in the triggered sample over the control sample indicates the presence of an erbB-3 activating ligand in the source containing a potential erbB-3 ligand. Alternatively, chimeric receptors, as shown in FIG. 11, can be utilized to screen for erbB-3 ligands. The erbB-3 activation can be ascertained by measuring the level of erbB-3 tyrosine phosphorylation in the triggered sample and in the control sample (an increase in the level of erbB-3 tyrosine phosphorylation correlates with an increase in the level of erbB-3 protein activation); measuring the level of cell growth in the triggered sample and in the control sample (wherein an increase in the level of cell growth correlates with an increase in the level of erbB-3 activation) or measuring the level of DNA synthesis for the cells in the triggered sample and in the control sample (an increase in the level of DNA synthesis for the cells correlates with an increase in the level of erbB-3 activation).

Similarly, the presence of an erbB-3 blocking or inhibiting ligand in a source containing a potential erbB-3 ligand can be detected by a) contacting a first sample of a cell line that expresses erbB-3 protein with the source containing a potential erbB-3 ligand for a time and under conditions sufficient to allow erbB-3 ligand contained in the source to bind to erbB-3 protein to form a blocked sample, wherein the cell line expresses erbB-3 protein having high level intrinsic tyrosine phosphorylation; b) contacting a second sample of the cell line with a control medium for the time and under the conditions as given in step a) to form a control sample; c) determining the level of erbB-3 activation in the blocked sample and in the control sample; and d) comparing the level of erbB-3 activation in the blocked sample with the level of erbB-3 activation in the control sample, wherein a decrease in activation in the blocked sample over the control sample indicates the presence of an erbB-3 blocking ligand in the source containing a potential erbB-3 ligand. Alternatively, chimeric receptors, as shown in FIG. 11, can be utilized to screen for erbB-3 blocking ligands.

In addition, the concentration of various ligands can be utilized to affect the erbB-3 activity. For example, a ligand which promotes erbB-3 activity at low concentrations can be administered or promoted to high concentrations which can inhibit erbB-3 activity.

This invention additionally provides a method of decreasing a biochemical or biological activity mediated by the erbB-3 receptor, comprising blocking the binding of an erbB-3 activating ligand with the erbB-3 receptor. The blocking can be accomplished by an antibody reactive with the ligand binding domain of the erbB-3 receptor or by an erbB-3 blocking ligand. Furthermore, a method of promoting a biochemical or biological activity mediated by the erbB-3 receptor, comprising contacting an erbB-3 activating ligand with the erbB-3 receptor is provided.

This invention also provides a method of detecting the overexpression of erbB-3 in a sample from a subject. The method comprises detecting the amount of erbB-3 in the sample and comparing the amount in the sample to the amount in an equivalent sample having normal expression, the presence of erbB-3 in a greater amount indicating overexpression of erbB-3. By "greater amount" is meant a statistically significant amount. Such amount depends on the conditions utilized and can readily be determined given the teachings set forth herein. Generally, a two-fold or greater increase would be predictive of overexpression. erbB-3 can be detected, for example, by detecting mRNA utilizing Northern hybridization, RNA dot blot, RNA slot blot, or in situ hybridization. erbB-3 can also be detected at the protein level utilizing, for example, Western blots, immunoprecipitation, immunohistochemistry, ELISA, and radioimmunoassay. Once overexpression is detected, the overexpression of erbB-3 can be correlated to a tumor. Such correlation can be used to diagnose a tumor or monitor the progression of a previously diagnosed tumor.

Also provided is a method of detecting the activation of erbB-3 in a test sample from a subject, comprising detecting the presence of phosphorylation of erbB-3, the presence of phosphorylation of erbB-3 indicating the presence of erbB-3 activation in the sample. This method can further comprise comparing the amount of erbB-3 phosphorylation in the test sample to the amount of erbB-3 phosphorylation in a sample from a normal subject and correlating an increase in phosphorylation in the test sample with the presence of a neoplastic condition in the subject. Such correlation can be used to diagnose a tumor or monitor the progression of a previously diagnosed tumor.

This invention further comprises a purified antibody specific for the human erbB-3 polypeptide having the amino acid sequence defined in FIG. 4 (SEQ ID NO:4) or the mature gp180$^{erbB-3}$ protein or a unique portion thereof, such as those polypeptides given by SEQ ID NOS:5–9. In this embodiment of the invention, the antibodies are monoclonal or polyclonal in origin, and are generated using erbB-3 receptor-related polypeptides or peptides from natural, recombinant or synthetic chemistry sources. The term "specific" refers to an erbB-3 antibody capable of binding or otherwise associating nonrandomly with an antigen of erbB-3 such that it does not cross react substantially with other antigens. These antibodies specifically bind to an erbB-3 protein which includes the sequence of such polypeptide. In other words, these antibodies bind substantially only to erbB-3 receptor proteins and not to erbB (EGFR) or erbB-2 proteins. Also, preferred antibodies of this invention bind to an erbB-3 protein when that protein is in its native (biologically active) conformation. For instance, MAb E-31 has been shown to detect the native erbB-3 protein.

Fragments of antibodies of this invention, such as Fab or F(ab)' fragments, which retain antigen binding activity and can be prepared by methods well known in the art, also fall within the scope of the present invention. Further, this invention comprises a pharmaceutical composition of the antibodies of this invention, or an active fragment thereof, which can be prepared using materials and methods for preparing pharmaceutical compositions for administration of polypeptides that are well known in the art and can be adapted readily for administration of the present antibodies without undue experimentation.

These antibodies and active fragments thereof, can be used, for example, for specific detection or purification of the novel erbB-3 receptor. Such antibodies could also be used in various methods known in the art for targeting therapeutic drugs, including cytotoxic agents, to tissues with high levels of erbB-3 receptors, for example, in the treatment of appropriate tumors with conjugates of such antibodies and cell killing agents. Accordingly, the present invention further relates to a method for targeting a therapeutic drug to cells having high levels of erbB-3 receptors, comprising the steps of i) conjugating an antibody specific for an erbB-3 receptor, or an active fragment of that antibody, to the therapeutic drug; and ii) administering the resulting conjugate to an individual with cells having high levels of erbB-3 receptors in an effective amount and by an effective route such that the antibody is able to bind to the erbB-3 receptors on those cells.

The antibody of this invention is exemplified by rabbit antisera containing antibodies which specifically bind to erbB-3 protein. Such receptor specific antisera are raised to synthetic peptides representing a unique portion of the erbB-3 amino acid sequence, having six or more amino acids in sequences which are sufficient to provide a binding site for an antibody specific for this portion of the erbB-3 polypeptide. Further, this unique portion of an erbB-3 amino acid sequence, of course, includes sequences not present in an erbB or an erbB-2 amino acid sequence, as predicted by the respective cDNA sequences. The erbB-3 specific antipeptide antibody of the present invention is exemplified by an anti-peptide antibody in polyclonal rabbit antiserum raised against any of the synthetic peptides given in SEQ ID NOS:5–9, which are derived from the predicted sequence of the erbB-3 polypeptide. The specific detection of erbB-3 polypeptide with antiserum raised against the peptide given in SEQ ID NO:5 is illustrated in mammalian cells transformed with an expression vector carrying a human erbB-3 cDNA (see FIG. 7). The antibody of this invention is further exemplified by erbB-3-specific monoclonal antibodies, such as the monoclonal antibody MAb E3-1, which was raised against the recombinantly expressed protein and is capable of detecting the native erbB-3 protein. MAb E3-1 specifically immunoprecipitated the mature 180 kDa erbB-3 protein from LTR-erbB-3 transfectants (FIG. 9A) and did not exhibit cross-reactivity with the EGFR or erbB-2 proteins.

Antibodies to peptides are prepared by chemically synthesizing the peptides, conjugating them to a carrier protein, and injecting the conjugated peptides into rabbits with complete Freund's adjuvant, according to standard methods of peptide immunization. For example, the peptide is synthesized by standard methods (Merrifield, R. B., 1963, *J. Amer. Soc.*, 85:2149) on a solid phase synthesizer. The crude peptide is purified by HPLC and conjugated to the carrier, keyhole limpet hemocyanin or bovine thyroglobulin, for example, by coupling the amino terminal cysteine to the carrier through a malcimido linkage according to well-known methods (e.g., Lerner R. A. et al., 1981, *Proc. Nat. Acad. Sci. USA*, 78:3403). In one standard method of peptide immunology, rabbits are immunized with 100 µg of the erbB-3 peptide-carrier conjugate (1 mg/ml) in an equal volume of complete Freund's adjuvant and then boosted at 10–14 day intervals with 100 µg of conjugated peptide in incomplete Freund's adjuvant. Additional boosts with similar doses at 10–14 day intervals are continued until antipeptide antibody titer, as determined, for example, by routine ELISA assays, reaches a plateau.

The antibody can be labeled with a detectable moiety or attached to a solid support by methods known in the art to facilitate detection of an antibody/antigen complex. Such a detectable moiety will allow visual detection of a precipitate or a color change, visual detection by microscopy, or automated detection by spectrometry or radiometric measurement or the like. Examples of detectable moieties include fluorescein and rhodamine (for fluorescence microscopy), horseradish peroxidase (for either light microscopy or electron microscopy and biochemical detection), biotin-streptavidin (for light or electron microscopy) and alkaline phosphatase (for biochemical detection by color change). The detection methods and moieties used can be selected, for example, from the list above or other suitable examples by the standard criteria applied to such selections (Harlow and Lane, *Antibodies: A Laboratory Manual*, Cold Spring Harbor Laboratory, Cold Spring Harbor, N.Y., 1988).

Thus, by following the teachings of the present disclosure, including application of generally known immunological methods cited herein, one of ordinary skill in the art is able to obtain erbB-3-specific antibodies and use them in a variety of immunological assays, for example, for diagnostic detection of unusually high or low expression in normal or tumor tissues. Thus, the present invention also relates to a bioassay for detecting an erbB-3 antigen in a biological sample comprising the steps of: i) contacting that sample with an antibody of the present invention specific for an erbB-3 polypeptide, under conditions such that a specific complex of that antibody and that antigen can be formed; and ii) determining the amount of that antibody present in the form of those complexes.

The present invention may be understood more readily by reference to the following detailed description of specific embodiments and the Examples and Figures included therein.

DESCRIPTION OF THE FIGURES

FIG. 3. Nucleotide sequence of the region of v-erbB homology in the human erbB-3 gene derived from human genomic DNA clone E3-1, in the 1.5 kbp region from the EcoRI to the PstI sites. This region contains three open reading frames bordered by splice junction consensus sequences (underlined). The predicted amino acid sequences of the three exons are shown in three letter code below the relevant DNA sequences;

FIG. 7A. Detection of erbB-3 polypeptide with the antiserum. FIG. 7B. Preincubation of the antiserum with homologous peptide. Antibody blocking indicates binding specificity. Lane 1: Selected cultures of NIH3T3 cells transfected with 1 µg LTR-erbB-3 expression vector. Lane 2: control NIH3T3 cells;

FIGS. 8A and 8B. Characterization of gp180$^{erbB-3}$ recombinantly expressed in NIH/3T3 cells. FIG. 8A. Immunoblot analysis of transfectants with erbB-3 peptide antisera MK4 and MK5 and peptide competition. FIG. 8B. Immunoprecipitation with MK5 antiserum of LTR-erbB-3 transfectants metabolically labeled for 2 h in the presence or absence of glycosylation inhibitor tunicamycin (1 µg/ml). FIG. 8C. Pulse-chase analysis: LTR-erbB-3 transfectants were pulse labeled for 15 min with 0.5 mCi each of [$^{35}$S] methionine and [$^{35}$S] cysteine and immediately lysed (0) or chased with 100 µg/ml each of unlabeled methionine and cysteine for the indicated time periods. 1×10$^7$ TCA-precipitable counts were immunoprecipitated from total lysates using MK5 antiserum;

FIG. 9A. Immunoprecipitation analysis of metabolically labeled LTR-erbB-3 transfectants with monoclonal antibody E3-1 and a non-immune control. FIGS. 9B–D. Indirect immunofluorescence: Formalin-fixed LTR-erbB-3 transfectants were incubated with MAb E3-1 (FIG. 9B) or non-immune IgG (FIG. 9C) and stained with a fluorescein-conjugated secondary antibody (100× original magnification). Indirect immunofluorescence with MAb E3-1 of native LTR-erbB-3 cells (FIG. 9D; 1000× original magnification);

DESCRIPTION OF SPECIFIC EMBODIMENTS

Figures 1A, 1B:
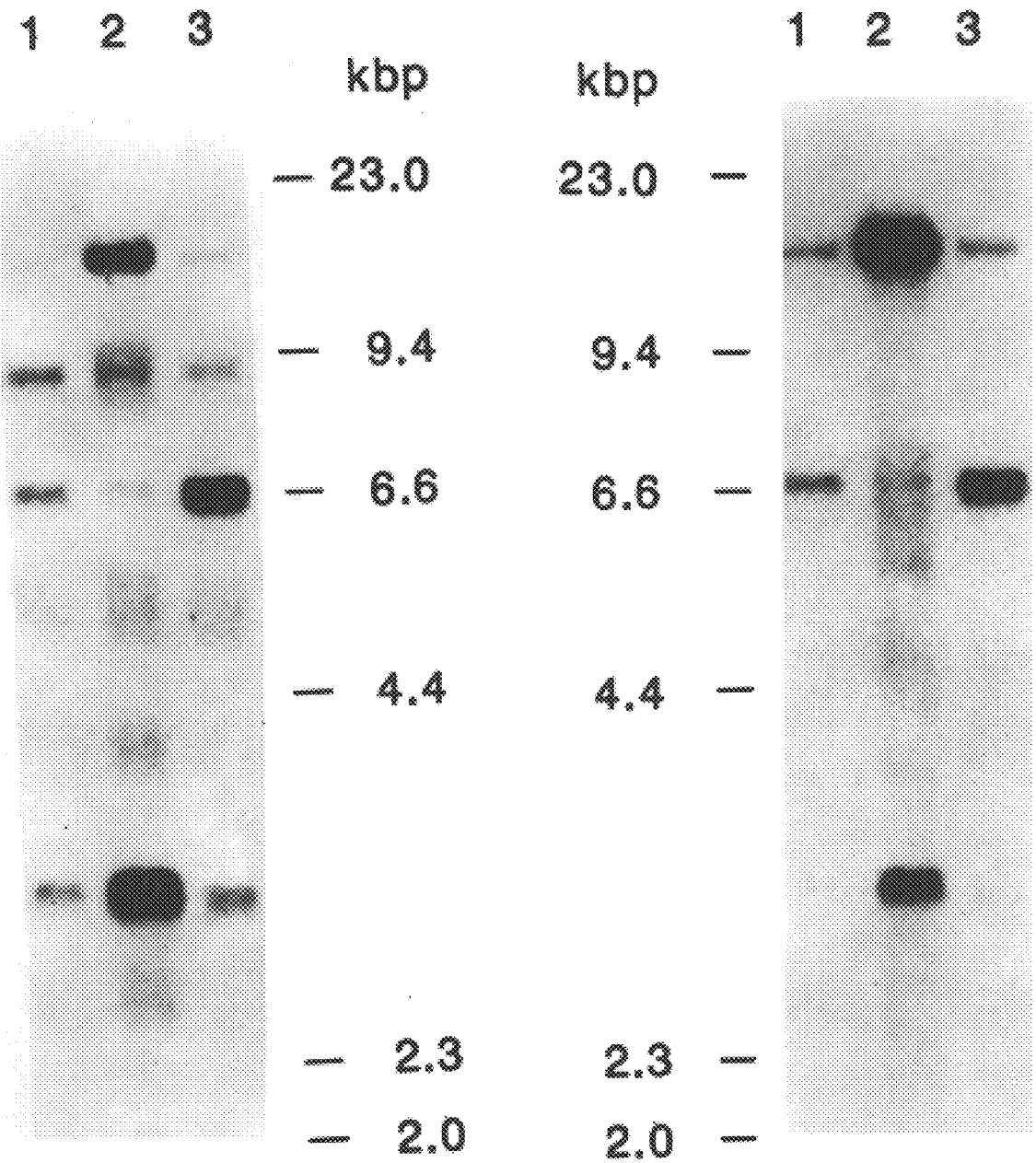
FIG. 1. Detection of v-erbB-related DNA fragments in DNAs from normal human thymus (lane 1), human mammary tumor lines MDA-MB468 (lane 2), and SK-BR-3 (lane 3). Hybridization was conducted at reduced (panel A) or intermediate (panel B) stringency conditions. The arrow denotes a novel 9 kilobase pair (kbp) erbB-related restriction fragment distinct from those of the EGFR gene (erbB) and erbB-2.

As used herein, the terms "polypeptide", "protein", "gene product", "antigen", "receptor", "receptor protein" and the like, when used in reference to erbB-3, encompass the erbB-3 amino acid functional sequence as given in SEQ ID NO:4, the mature erbB-3 glycoprotein, gp180$^{erbB-3}$, and these entities modified by other post-translational modifications, such as glycosylation or tyrosine phosphorylation. However, as is common in the art, the term "erbB-3 polypeptide" typically refers to the sequence as given in SEQ ID NO:4 while the remaining terms typically refer to gp180$^{erbB-3}$.

The identification of a third member of the erbB-EGF receptor family of membrane spanning tyrosine kinases and the cloning of its full length coding sequence is described the Examples herein. The presence of apparent structural domains resembling those of the EGF receptor suggests the existence of an extracellular binding site for a ligand. The structural relatedness of the extracellular domain of the erbB-3 receptor with that of the EGF receptor indicates that one or more of an increasing number of EGF-like ligands (Shoyab, M., Plowman, G. D., McDonald, V. L. Bradley, J. G. & Todaro, G. J., 1989, *Science* 243:1074–1076) interacts with the erbB-3 product. Accordingly, the erbB-3 gene is expected to play important roles in both normal and neoplastic processes, as is known for the EGFR and erbB-2 genes.

Despite extensive collinear homology with the EGF receptor and erbB-2, distinct regions within the predicted erbB-3 coding sequence revealed relatively higher degrees of divergence. For example, its carboxyl terminal domain failed to exhibit significant collinear identity scores with either erbB-2 or EGFR. The divergence at the carboxyl terminus also accounts for minor size differences among the three polypeptides of erbB-3, erbB-2, and EGFR, which possess estimated molecular weights of 148 kilodaltons (kd), 138 kDa, and 131 kd, respectively. Within the tyrosine kinase domain, which represents the most conserved region of the predicted erbB-3 protein, a short stretch of 29 amino acids closer to the carboxyl terminus than the ATP binding site differed from regions of the predicted erbB-2 and EGFR coding sequence in 28 and 25 positions, respectively. Such regions of higher divergence in their cytoplasmic domains are likely to confer different functional specificity to these closely related receptor-like molecules. Thus, mutations or other alterations in expression of the erbB-3 gene are likely to cause cancers or genetic disorders different from those associated with such defects in the erbB and erbB-2 genes.

Chromosomal mapping localized erbB-3 to human chromosome 12 at the q11–13 locus, whereas the related EGFR and erbB-2 genes are located at chromosomal sites 7p12–13 and 17p12–21.3, respectively. Thus, each gene appears to be localized to a region containing a different homeobox and a different collagen chain gene locus. Keratin type I and type II genes also map to regions of 12 and 17, respectively, consistent with the different localizations of erbB-3 and erbB-2, respectively. Thus, the DNA segments of the present invention represent novel probes to aid in genetic mapping of any heritable diseases which are associated with chromosomal aberrations in the vicinity of the 12q11–13 locus.

There is evidence for autocrine as well as paracrine effectors of normal cell proliferation. The former are factors that are produced by the same cells upon which they stimulate cell proliferation, whereas the latter factors are secreted by cells other than those that are affected by those factors. However, the inherent transforming potential of autocrine growth factors suggests that growth factors most commonly act on their target cell populations by a paracrine route. The present survey of erbB-3 gene expression indicates its normal expression in cells of epithelial and neuro-ectodermal derivation. Comparative analysis of the three erbB receptor-like genes in different cell types of epidermal tissue revealed that keratinocytes expressed all three genes. In contrast, melanocytes and stromal fibroblasts specifically lacked EGFR and erbB-3 transcripts, respectively. Thus, melanocytes and stromal fibroblasts may be sources of paracrine growth factors for EGFR and erbB-3 products, respectively, that are expressed by the other cell types residing in close proximity in epidermal tissues.

Given that both erbB and erbB-2 have been causally implicated in human malignancy, the present findings (Example 5) that the erbB-3 transcript is overexpressed in a significant fraction of human mammary tumor cell lines indicates that this new member of the EGFR receptor family also plays an important role in some human malignancies.

Characterization of the human erbB-3 gene product, gp180$^{erbB-3}$, shows that it is a transmembrane glycoprotein exhibiting properties characteristic of a receptor-like tyrosine kinase. The recombinant human erbB-3 protein shared identical electrophoretic mobility with the natural erbB-3 product expressed in human breast tumor cell lines. Moreover, both recombinant and endogenously expressed gp180$^{erbB-3}$ was recognized by different antibodies directed against distinct epitopes, such as monoclonal (i.e., Mab E3-1) and peptide antibodies directed against epitopes in the extracellular and carboxyl-terminal domains. The 145 kDa erbB-3 polypeptide precursor conformed with predicted erbB-3 encoded protein following cleavage of its signal sequence. Finally, demonstration of its inherent signaling properties established functional integrity of recombinantly expressed gp180$^{erbB-3}$.

Although the erbB-3 tyrosine kinase domain shares greater than 60% amino acid identity with the EGFR and erbB-2 proteins, single amino acid substitutions differences in highly conserved residues shared among known tyrosine kinases raised a question as to whether erbB-3 harbors intrinsic catalytic activity involved in signal propagation instead of signal attenuation as has been postulated for certain receptor tyrosine kinase-like molecules (Chou et al., Proc. Natl. Acad. Sci. USA 88:4897 (1991)). Most notably, codon 834 within the tyrosine kinase domain predicts asparagine in erbB-3, while aspartate is present at this position in essentially all known protein kinases. Moreover, substitution of asparagine for aspartate in this position abolishes c-kit and v-fps tyrosine kinase activity. The present characterization of the erbB-3 cytoplasmic domain demonstrates not only its catalytic function but also the ability to transduce a mitogenic signal as well. gp180$^{erbB-3}$ demonstrated autokinase activity in vitro and, in some cell lines, tyrosine phosphorylation in vivo. Moreover, EGF-dependent activation of gp180$^{EGFR/erbB-3}$ was associated both with mitogenic signaling and in vivo tyrosine phosphorylation of the chimeric receptor. All of these findings imply that the erbB-3 protein represents a biologically active membrane spanning receptor capable of transducing a mitogenic signal in a ligand-dependent manner. Thus, the erbB-3 gene encodes a membrane spanning molecule possessing all the properties of a functional growth receptor.

Constitutive activation of erbB-3 catalytic activity was demonstrated in LTR-erbB-3 transfectants. These results raise the possibility that NIH/3T3 cells may express an erbB-3 ligand. If so, this putative ligand would unlikely interact with the EGFR, since overexpression of the latter in NIH/3T3 cells is not associated with its chronic tyrosine phosphorylation in the absence of exogenous EGF. This invention further established that EGF neither enhanced in vivo tyrosine phosphorylation of gp180$^{erbB-3}$ nor elicited a mitogenic response in LTR-erbB-3 cells. Additional ligands of the EGF family, including TGFα, amphiregulin, and HB-EGF, have also failed to stimulate gp180$^{erbB-3}$ tyrosine phosphorylation or DNA synthesis in LTR-erbB-3 cells. While a low affinity interaction of known EGF-related ligands for gp180$^{erbB-3}$ cannot be excluded, these findings indicated that erbB-3 and EGFR proteins possess distinct ligand specificities. The ability to trigger the erbB-3 catalytic domain in the EGFR/erbB-3 chimeric molecule should make it possible to more readily identify its substrates as well as to compare them with those of its closely related family members.

Based upon this invention's demonstration that the erbB-3 protein is both catalytically active and can elicit a proliferative response in NIH/3T3 cells, the instant findings of its chronic activation in some human breast tumor cells suggest its contribution to the malignant phenotype in such tumors. Analogous evidence has implicated overexpression associated with gene amplification of both EGFR and erbB-2 in a variety of tumors as well. In such tumors, there is precedence for activation of receptor kinase activity by mechanisms involving autocrine loops as well as genetic alterations affecting regulatory or coding sequences.

Both EGFR and erbB-2 genes have been implicated as oncogenes based upon demonstration of their overexpression and constitutive activation in various human tumors. The results of this invention argue strongly that the most recently identified family member, erbB-3, is activated in some human breast tumors. Overexpression of the erbB-3 protein did not invariably correlate with its chronic tyrosine phosphorylation. Hence, erbB-3 activation may involve autocrine stimulation or subtle genetic alterations. In addition to breast tumors, expression of the erbB-3 transcript has been observed in a wide range of human carcinomas, including colon, lung, kidney, pancreas, and skin. These findings prompt the search for evidence of erbB-3 activation as an oncogene in these other common human cancers.

EXAMPLE 1

Identification of a Human DNA Fragment Related to the erbB-3 proto-oncogene Family In an effort to detect novel erbB-related genes, human genomic DNA was cleaved with a variety of restriction endonucleases and subjected to Southern blot analysis with v-erbB as a probe. Normal mammary epithelial cells AB589 (Walen, K. H. & Stampfer, M. R., 1989, Cancer. Genet. Cytogenet. 37:249–261) and immortalized keratinocytes RHEK have been described previously (Rhim, J. S., Jay, G., Arnstein, P., Price, F. M., Sanford, K. K. & Aaronson, S. A., 1985, Science 227:1250–52). Normal human epidermal melanocytes (NHEM) and keratinocytes (NHEK) were obtained from Clonetics. Sources for human embryo fibroblasts (Rubin, J. S., Osada, H., Finch, P. W., Taylor, W. G., Rudikoff, S., & Aaronson, S. A., 1989, Proc. Nat. Acad. Sci. USA 86:802–806) or mammary tumor cell lines SK-BR-3, MDA-MB468, MDA-MB453, and MDA-MB415 (Kraus, M. H., Popescu, N. C., Amsbaugh, S. C. & King, C. R., 1987, EMBO. J. 6:605–610) have been described. For nucleic acid RNA hybridization, DNA and RNA were transferred to nitrocellulose membranes as previously described (Kraus, M. H., et al., 1987, supra). High stringency hybridization was conducted in 50% formamide and 5×SSC at 42° C. Filters were washed at 50° C. in 0.1×SSC. Reduced stringency hybridization of DNA was carried out in 30% formamide followed by washes in 0.6×SSC, while intermediate stringency was achieved by hybridization in 40% formamide and washing in 0.25×SSC. For the specific results depicted in FIG. 1, DNAs were restricted with SacI and hybridized with probe specific for an oncogenic viral form of the erbB gene, v-erbB, spanning from the upstream BamHI site to the EcoRI site in the avian erythroblastosis proviral DNA (Vennstrom, B., Fanshier, L., Moscovici, C. & Bishop, J. M., 1980, J Virol. 36:575–585).

Under reduced stringency hybridization, four SacI restriction fragments were detected. Two were identified as EGFR gene fragments by their amplification in the mammary tumor cell line MDA-MB468 (FIG. 1A, lane 1,2) known to contain EGFR gene amplification and one as an erbB-2 specific gene fragment due to its increased signal intensity in another mammary tumor cell line, SK-BR-3, known to have erbB-2 amplified (FIG. 1A, lane 1,3). However, a single 9 kbp SacI fragment exhibited equal signal intensities in DNAs from normal human thymus, SK-BR-3 and a line with high levels of EGFR, A431 (FIG. 1A). When the hybridization stringency was raised by 7° C., this fragment did not hybridize, whereas EGFR and erbB-2 specific restriction fragments were still detected with v-erbB as a probe (FIG. 1B). Taken together, these findings suggested the specific detection of a novel v-erbB-related DNA sequence within the 9 kbp SacI fragment.

EXAMPLE 2

Cloning of the Human DNA Fragment Related to erbB

For further characterization, a normal human genomic library was prepared from SacI cleaved thymus DNA enriched for 8 to 12 kbp fragments. For convenience, bacteriophage λsep-lac5 was obtained from L. Prestidge and D. Hogness (Stanford University); many other cloning vectors derived from phage λ or other genomes can be used for cloning this DNA fragment according to standard recombinant DNA methods that are well known in the art. Purified phage DNA was subjected to cos-end ligation, restriction with SacI, and fractionation in a continuous 10–40% sucrose gradient. A genomic library was prepared by ligating SacI restriction fragments of normal human thymus DNA in the molecular weight range of 8 kbp to 12 kbp (isolated by sucrose gradient sedimentation) with the purified phage arms. Ten recombinant clones detected by v-erbB under reduced stringency conditions did not hybridize with human EGFR or erbB-2 cDNA probes at high stringency. As shown in the restriction map of a representative clone with 9 kbp insert, the region of v-erbB homology was localized by hybridization analysis to a 1.5 kbp segment spanning from the EcoRI to the downstream PstI site.

Figure 2:
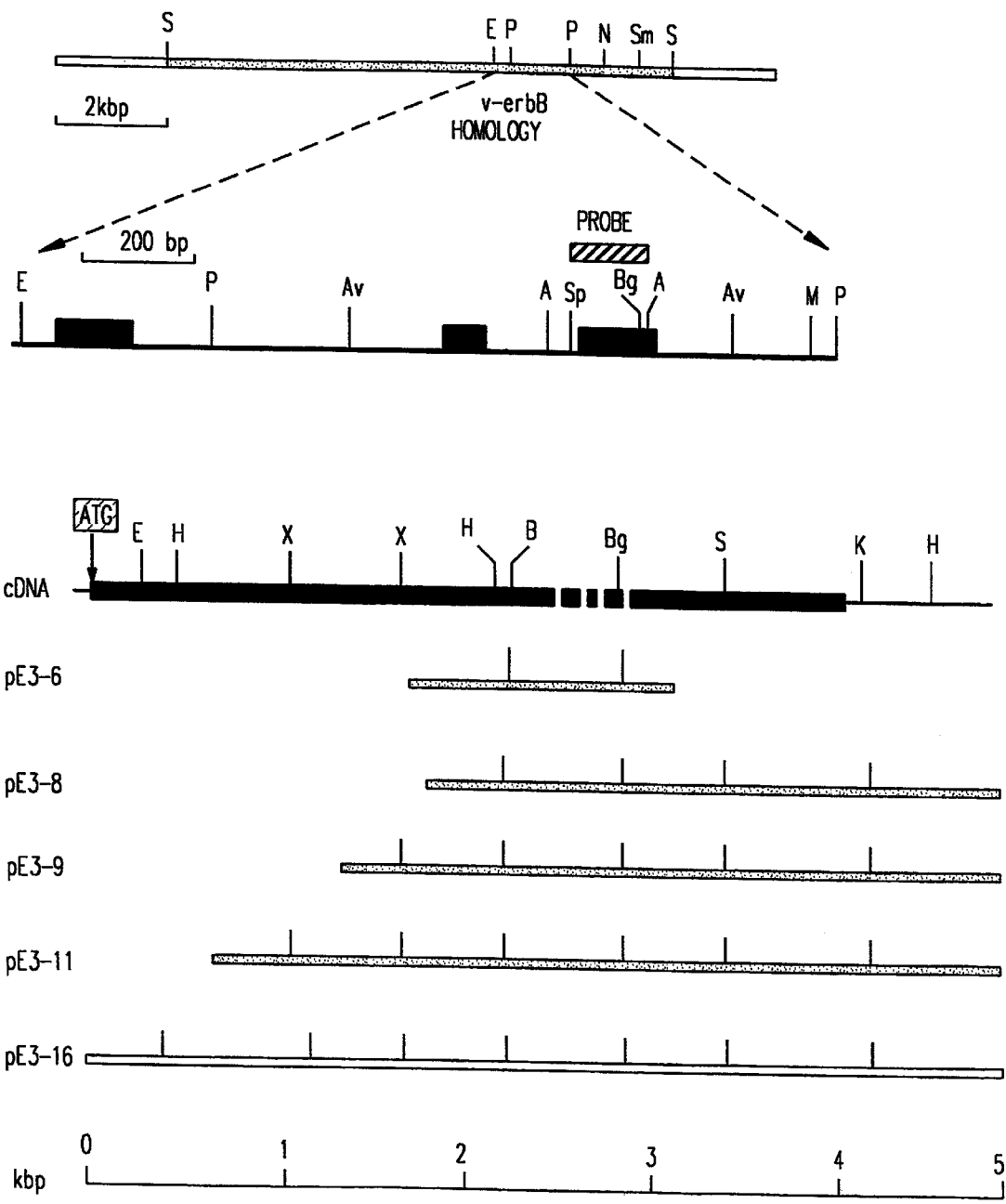
FIG. 2. Genomic and cDNA cloning of erbB-3. The region of (v-erbB) homology within the genomic 9 kbp SacI insert of λE3-1 was subcloned into the plasmid pUC (pE3-1) and subjected to nucleotide sequence analysis. The three predicted exons are depicted as solid boxes. erbB-3 cDNA clones were isolated from oligo dT-primed libraries of mRNAs from normal human placenta (shaded bars) and the breast tumor cell line MCF-7 (open bar). The entire nucleotide sequence was determined for both strands on erbB-3 complementary DNA from normal human placenta and upstream of the 5' XhoI site on pE3-16. The coding sequence is shown as a solid bar and splice junctions of the three characterized genomic exons are indicated by vertical white lines. Solid lines in the cDNA map represent untranslated sequences. Restriction sites: A=AccI, Av=AvaI, B=BamHI, Bg=BglII, E=EcoRI, H=HindIII, K=KpnI, M=MstII, P=PstI, S=SacI, Sm=SmaI, Sp=SpeI.

The nucleotide sequence of a portion of a clone of the novel human genomic DNA fragment related to erbB was determined for both DNA strands by the dideoxy chain termination method (Sanger, F., Nicklen, S. & Coulson, A. R., 1977, *Proc. Nat. Acad Sci. USA.* 74:5463–67) using supercoiled plasmid DNA as template. The nucleotide sequence was assembled and translated using IntelliGenetics software. Amino acid sequence comparison was performed with the alignment program by Pearson and Lipman (Pearson, W. R. & Lipman, D. J., 1988, supra) as implemented on the computers of the NCI Advanced Scientific Computing Laboratory. Hydrophobic and hydrophilic regions in the predicted protein were identified according to Kyte and Doolittle (Kyte, J. & Doolittle, R. F., 1982, *J Mol. Biol.* 157:105–132). Nucleotide sequence analysis revealed that the region of v-erbB homology in the 1.5 kbp segment from the EcorRI to the PstI contained three open reading frames bordered by splice junction consensus sequences (FIG. 2). Computerized comparisons of the predicted amino acid sequence of these three open reading frames with other known proteins revealed the highest identity scores of 64% to 67% to three regions which are contiguous in the tyrosine kinase domains of v-erbB, as well as human EGFR and erbB-2 proteins. Furthermore, all splice junctions of the three characterized exons in the new gene were conserved with erbB-2. Amino acid sequence homology to other known tyrosine kinases was significantly lower, ranging from 39% to 46%.

A single 6.2 kb specific mRNA was identified by Northern blot analysis of human epithelial cells using the 150 bp SpeI-AccI exon-containing fragment as probe (FIG. 2). Under the stringent hybridization conditions employed, this probe detected neither the 5 kb erbB-2 mRNA nor the 6 kb and 10 kb EGFR mRNAs. All of these findings suggested that the present work has identified a new functional member of the erbB proto-oncogene family, which tentatively has been designated as erbB-3.

EXAMPLE 3

Cloning and Characterization of cDNAs for the mRNA of the Human erbB-3 Gene

In an effort to characterize the entire erbB-3 coding sequence, overlapping cDNA clones were isolated from oligo dT-primed cDNA libraries from sources with known erbB-3 expression, utilizing gene-specific genomic exons or cDNA fragments as probes. In brief, an oligo dT-primed human placenta cDNA library in λgt11 was obtained from Clontech. MCF-7 cDNA was prepared by first strand synthesis from 5 μg poly $A^+$ RNA using an oligo dT containing linker-primer and Mo-MuLV reverse transcriptase, followed by second strand synthesis with DNA polymerase I, RNaseH, and subsequent T4 DNA polymerase treatment. Double-stranded cDNA was directionally cloned into the SfiI site of λpCEV9 using specific linker-adapter oligonucleotides (Miki, T., Matusi, T., Heidaran, M. A. & Aaronson, S. A., 1989, *Gene* 83:137–146; see also, U.S. application Ser. No. 07/386,053 of Miki et al., filed Jul. 28, 1989). Following plaque purification, phage DNA inserts were subcloned into pUC-based plasmid vectors for further characterization. The clones were initially characterized by restriction analysis and hybridization to the mRNA, and were subsequently subjected to nucleotide sequence analysis. Clones designated pE3-6, pE3-8, pE-9, and pE3-11 carrying inserts with molecular weights ranging from 1.3 kbp to 4.3 kbp were isolated from a human placenta library, whereas the pE3-16 clone containing a 5 kbp insert was obtained by screening the MCF-7 cDNA library with the upstream most coding sequence of pE3-11 as a probe. The clones pE3-8, pE3-9, pE3-11, and pE3-16 contained identical 3' ends terminating in a poly A stretch (FIG. 2).

The complete coding sequence of erbB-3 was contained within a single long open reading frame of 4080 nucleotides extending from position 46 to an in-frame termination codon at position 4126. The most upstream ATG codon at position 100 was the likely initiation codon, as it was preceded by an in-frame stop codon at nucleotide position 43 and fulfilled the criteria of Kozak for an authentic initiation codon. The open reading frame comprised 1342 codons predicting a 148 kDa polypeptide. Downstream from the termination codon, multiple stop codons were present in all frames. As shown in SEQ ID NO:4, the deduced amino acid sequence of the erbB-3 polypeptide predicted a transmembrane receptor tyrosine kinase most closely related to EGFR and erbB-2. A hydrophobic signal sequence of erbB-3 was predicted to comprise the 19 amino-terminal amino acid residues. Cleavage of this signal sequence between glycine at position 19 and serine at position 20 would generate a processed polypeptide of 1323 amino acids with an estimated molecular weight of 145 kDa. A single hydrophobic membrane spanning domain encompassing 21 amino acids was identified within the coding sequence separating an extracellular domain of 624 amino acids from a cytoplasmic domain comprising 678 amino acids (SEQ ID NO:4).

The putative erbB-3 ligand-binding domain was 43% and 45% identical in amino acid residues with the predicted erbB-2 and EGFR protein, respectively. Within the extracellular domain, all 50 cysteine residues of the processed erbB-3 polypeptide were conserved and similarly spaced when compared to the EGFR and erbB-2. Forty-seven cysteine residues were organized in two clusters containing 22 and 25 cysteines respectively, a structural hallmark of this tyrosine kinase receptor subfamily (see, for example, Yamamoto, T., Ikawa, S., Akiyama, T., Semba, K., Nomura, N., Miyajima, N., Saito, T. and Toyoshima, K., 1986, *Nature* 319:230–234). Ten potential N-linked glycosylation sites were localized within the erbB-3 extracellular domain. In comparison with the EGFR and erbB-2 proteins, five and two of these glycosylation sites were conserved, respectively. Among these, the site proximal to the transmembrane domain was conserved among all three proteins (SEQ ID NO:4).

Within the cytoplasmic domain, a core of 277 amino acids from position 702 through 978 revealed the most extensive homology with the tyrosine kinase domains of EGFR and erbB-2. In this region 60% or 62% of amino acid residues were identical and 90% or 89% were conserved, respectively. This stretch of amino acid homology coincides with the minimal catalytic domain of tyrosine kinases (Hanks, S. K., Quinn, A. M. & Hunter, T., 1988, *Science* 241:42–52).

Figure 4B:
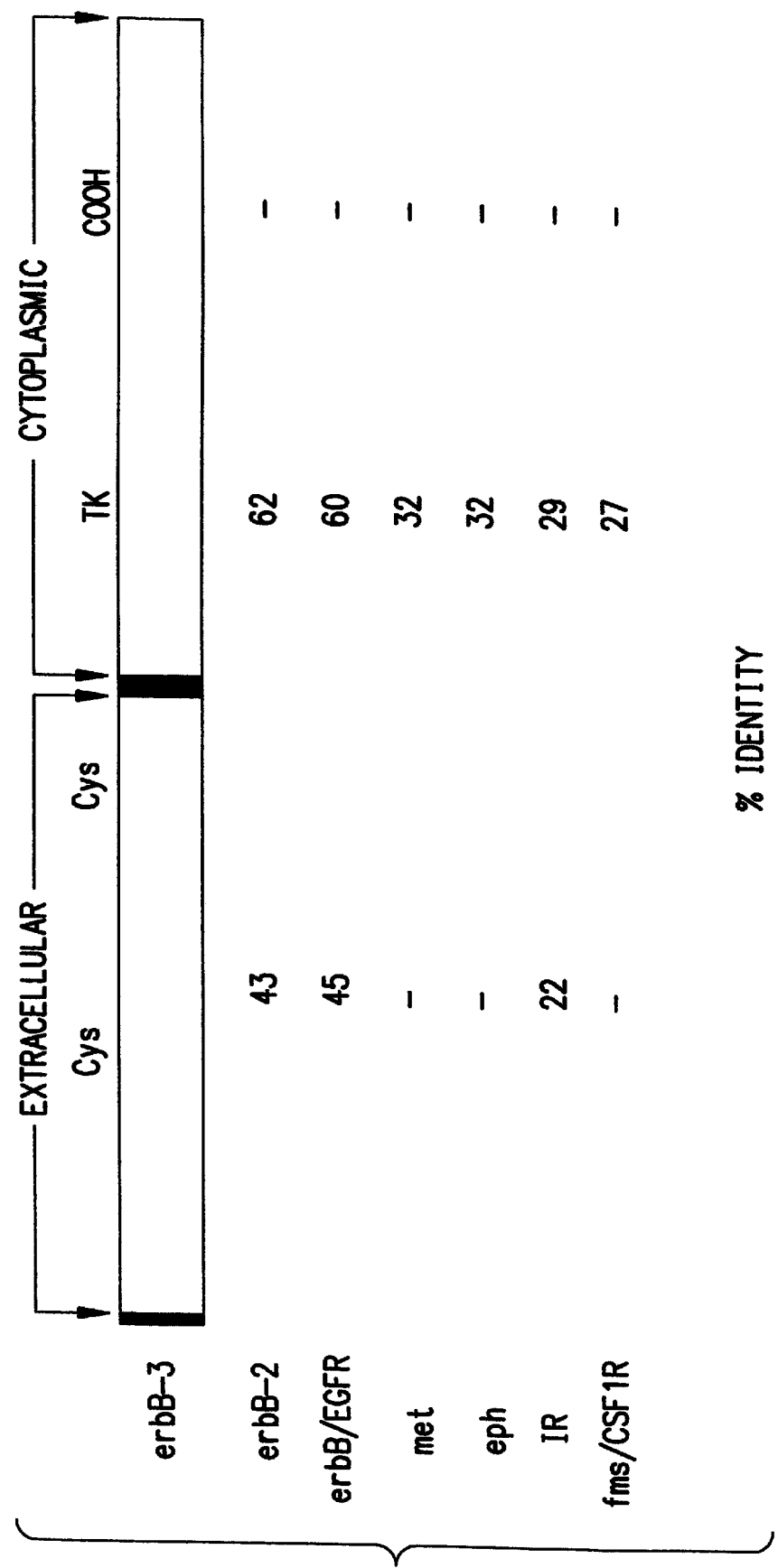
FIG. 4. Comparison of the predicted amino acid sequence of the erbB-3 polypeptide with other receptor-like tyrosine kinases. The amino acid sequence is shown in single letter code and is numbered on the right. The putative extracellular domain (light shading) extends between the predicted signal sequence (solid box) at the amino-terminus and a single hydrophobic transmembrane region (solid box) within the polypeptide. The two cysteine clusters (Cys) in the extracellular domain and the predicted tyrosine kinase domain (TK) within the cytoplasmic portion of the polypeptide are outlined by dark-shading. The putative ATP-binding site at the amino-terminus of the TK domain is circled. Potential autophosphorylation sites within the carboxyl-terminal domain (COOH) are indicated by asterisks. Potential N-linked glycosylation sites (→) are marked above the amino acid sequence. The percentage of amino acid homology of erbB-3 in individual domains with erbB-2, EGFR, met, eph, insulin receptor (IR), and fms is listed below. Less than 16% dentity is denoted by (−)

There was significantly lower homology with other tyrosine kinases (FIG. 4). The consensus sequence for an ATP-binding site (GxGxxG, Hanks, S. K. et al., 1988, supra) was identified at amino acid positions 716 through 721. This sequence as well as a lysine residue located 21 amino acid residues further toward the carboxyl terminus was conserved between the three erbB-related receptors. Taken together these findings defined the region between amino acid position 702 and 978 as the putative catalytic domain of the erbB-3 protein (SEQ ID NO:4).

The most divergent region of erbB-3 compared to either EGFR or erbB-2 was its carboxyl terminus comprising 364 amino acids. This region showed a high degree of hydrophilicity and the frequent occurrence of proline and tyrosine residues. Among these tyrosine residues, those at positions 1197, 1199, and 1262 matched closest with the consensus sequence for putative phosphorylation sites. The peptide sequence YEYMN (SEQ ID NO:12), encompassing tyrosine 1197 and 1199, was repeated at positions 1260–1264 and was at both locations surrounded by charged residues, providing an environment of high local hydrophilicity. These observations render tyrosines 1197, 1199 and 1262 likely candidates for autophosphorylation sites of the erbB-3 protein.

EXAMPLE 4

Chromosomal Mapping of the Human erbB-3 Gene

Figure 5:
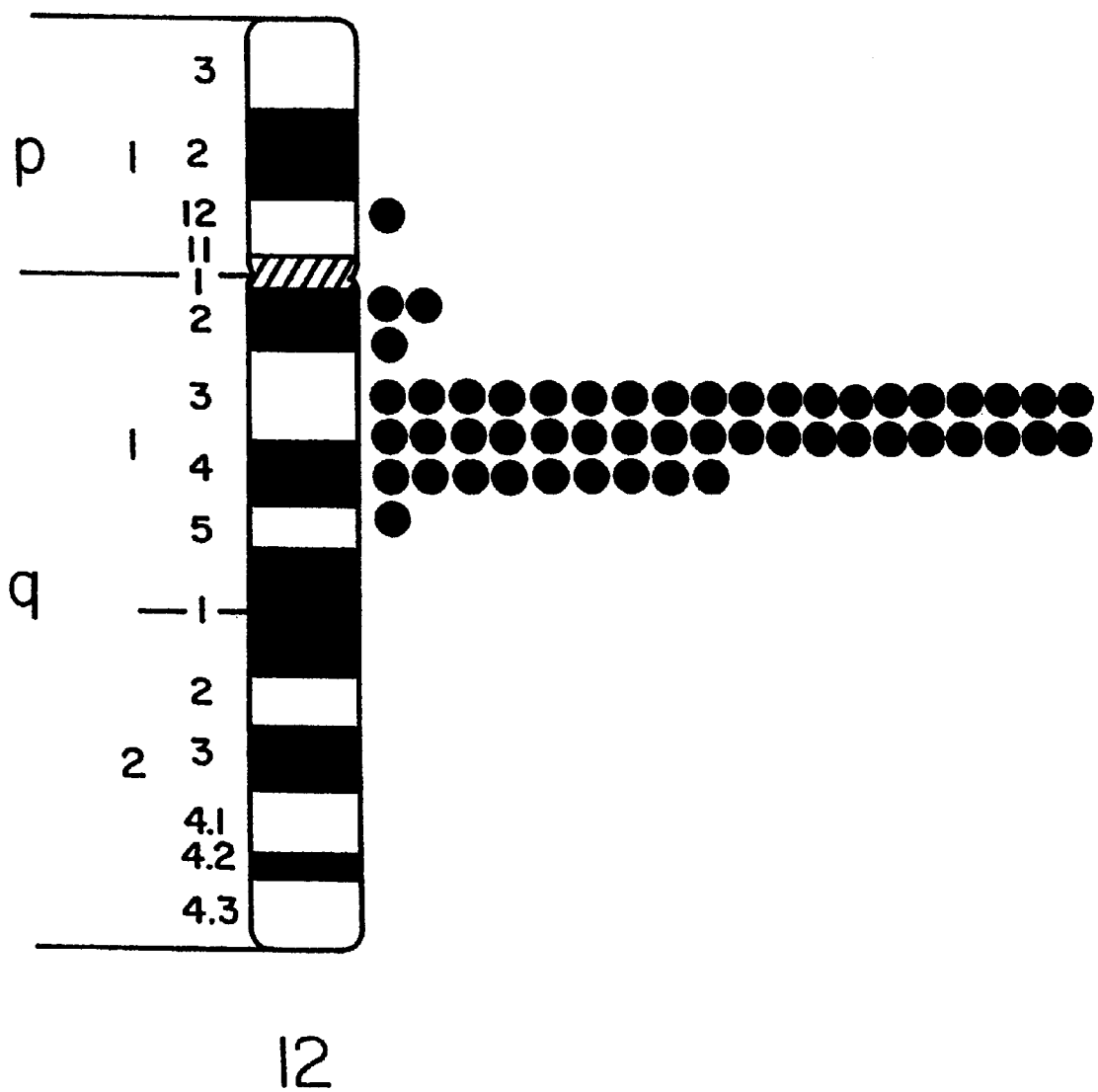
FIG. 5. Assignment of the genomic locus of erbB-3 to human chromosomal locus 12q13. A total of 142 grains were localized on the 400-band ideogram. As depicted in the diagram, specific labeling of chromosome 12 was observed, where 38 out of 51 grains were localized to band q13.

The chromosomal location of the erbB-3 gene was determined by in situ hybridization (Popescu, N. C., King, C. R. & Kraus, M. H., 1989, *Genomics* 4:362–366) with a $^3$H-labeled plasmid containing the amino-terminal erbB-3 coding sequence. A total of 110 human chromosome spreads was examined prior and subsequent to G banding for identification of individual chromosomes. A total of 142 grains was localized on a 400-band ideogram. Specific labeling of chromosome 12 was observed, where 38 out of 51 grains were localized to band q13 (FIG. 5). Thus, the genomic locus of erbB-3 was assigned to 12q13. In this region of chromosome 12, several genes have previously been mapped including the melanoma-associated antigen ME491, histone genes and the gene for lactalbumin. In addition, two proto-oncogenes, int-1 and gli are located in close proximity to erbB-3.

EXAMPLE 5 erbB-3 Expression in Normal and Malignant Human Cells

To investigate its pattern of expression, a number of human tissues were surveyed for the erbB-3 transcript. The 6.2 kb erbB-3 specific mRNA was observed in term placenta, postnatal skin, stomach, lung, kidney, and brain, while it was not detectable in skin fibroblasts, skeletal muscle or lymphoid cells. Among the fetal tissues analyzed, the erbB-3 transcript was expressed in liver, kidney, and brain, but not in fetal heart or embryonic lung fibroblasts. These observations indicate the preferential expression of erbB-3 in epithelial tissues and brain.

ErbB-3 expression was also investigated in individual cell populations derived from normal human epithelial tissues including keratinocytes, glandular epithelial cells, melanocytes, and fibroblasts. For comparison levels of EGFR and erbB-2 transcripts were analyzed. As shown in Table 1, erbB-3 mRNA levels were relatively high in keratinocytes, comparable with those of erbB-2 and EGFR in these cells. Lower, but similar expression levels of each transcript were detected in cells derived from glandular epithelium. These findings are consistent with growth regulatory roles of all three receptor-like molecules in squamous and glandular epithelium. Whereas erbB-2 and EGFR transcripts were also readily observed in normal fibroblasts, the same cells lacked detectable erbB-3 mRNA. In contrast, normal human melanocytes, which expressed both erbB-3 and erbB-2 at levels comparable with human keratinocytes, lacked detectable EGFR transcripts. Thus, the expression patterns of these receptor-like molecules were different in specialized cell populations derived from epidermal tissues.

TABLE 1

Normal expression pattern of human erbB gene family members

| Cell Source of Transcripts | Gene | Relative RNA levels |
|---|---|---|
| Embryonic fibroblast (M426) | erbB-3 | – |
|  | erbB-2 | + |
|  | EGF-R | + |
| Skin fibroblast (501T) | erbB-3 | – |
|  | erbB-2 | + |
|  | EGF-R | + |
| Immortal keratinocyte (RHEK) | erbB-3 | ++ |
|  | erbB-2 | ++ |
|  | EGF-R | ++ |
| Primary keratinocyte (NHEK) | erbB-3 | + |
|  | erbB-2 | + |
|  | EGF-R | ++ |
| Glandular epithelium (AB589) | erbB-3 | (+) |
|  | erbB-2 | (+) |
|  | EGF-R | (+) |
| Melanocyte (NHEM) | erbB-3 | ++ |
|  | erbB-2 | ++ |
|  | EGF-R | – |

Replicate Northern blots were hybridized with equal amounts (in cpm) of probes of similar specific activities for erbB-3, erbB-2, and EGFR, respectively. Relative signal intensities were estimated: – not detectable, (+) weakly positive, + positive, ++ strongly positive.

Figure 6A:
FIGS. 6A and 6B. Elevated erbB-3 transcript levels in human mammary tumor cell lines. A Northern blot containing 10 µg total cellular RNA from AB589 mammary epithelial cells (lane 1), as well as mammary tumor cell lines MDA-MB415 (lane 2) and MDA-MB453 (lane 3) was hybridized with an erbB-3 cDNA probe (FIG. 6A). Following signal decay the same blot was rehybridized with a human β-actin cDNA probe (FIG. 6B) (Gunning, P., Ponte, P., Okayama, H., Engel, J., Blau, H. & Kedes, L., 1983, *Mol. Cell Biol.* 3:787–795)
Figure 6B:
Figures 7A, 7B:
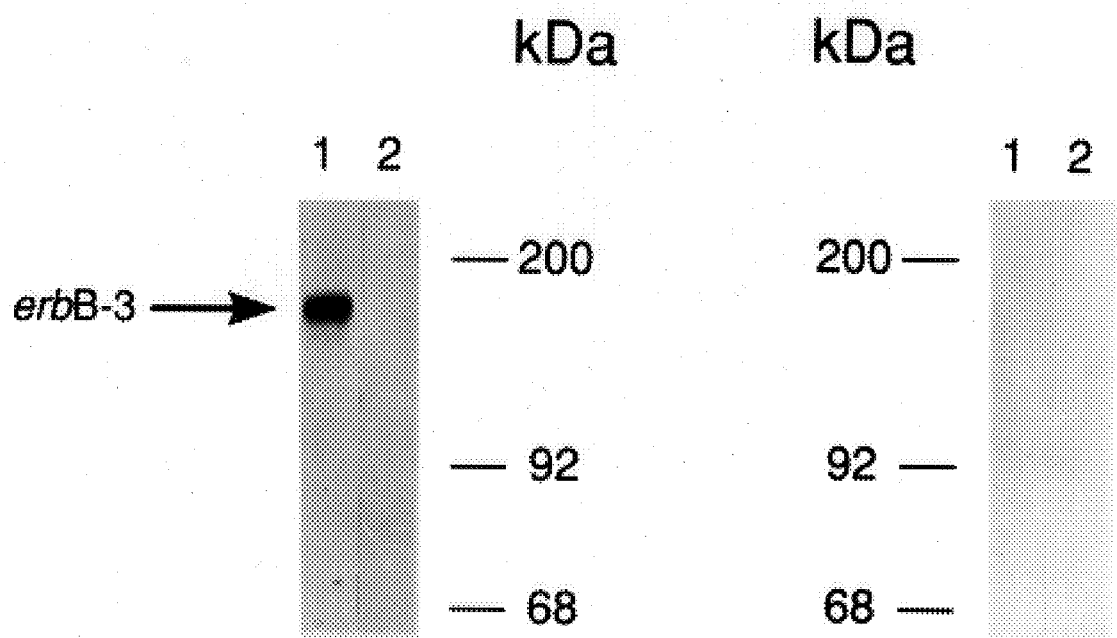
FIGS. 7A and 7B. Expression of a human erbB-3 polypeptide in cells transformed by a cDNA segment as detected by an erbB-3-specific anti-peptide antiserum. Cellular lysates (100 µg of each sample) were electrophoresed and transferred to nitrocellulose membranes for analysis by Western blotting.

To search for evidence of erbB-3 involvement in the neoplastic process, erbB-3 mRNA levels in a series of human tumor cell lines were surveyed. The erbB-3 transcript was detected in 36 of 38 carcinomas and in 2 of 12 sarcomas while 7 tumor cell lines of hematopoietic origin lacked measurable erbB-3 mRNA. Markedly elevated levels of a normal-sized transcript were observed in 6 out of 17 tumor cell lines derived from human mammary carcinomas. By Southern blot analysis, neither gross gene rearrangement nor amplification was detected in the cell lines. FIG. 6A shows the results of Northern blot analysis with control AB589 nonmalignant human mammary epithelial cells (lane 1) and two representative human mammary tumor lines, MDA-MB415 (lane 2) and MDA-MB453 (lane 3). Hybridization of the same filter with human β-actin probe (FIG. 6B) verified actual levels of mRNA in each lane. Densitometric scanning indicated that the erbB-3 transcript in each tumor cell line was elevated more than 100 fold above that of the control cell line. Thus, overexpression of this new member of the erbB family, as in the case of the EGFR and erbB-2 genes, is likely to play an important role in some human malignancies.

EXAMPLE 6

Further Characterization of the normal erbB-3 gene product

The pZIPneo expression vector (Cepko et al, *Cell* 37:1053 (1984)) was modified by introduction of a unique Sal I cloning site. Following deletion of the Sal I site in the tetracycline resistance gene, the synthetic oligonucleotides 5'-GATCTCGAGTCGAC-3' (SEQ ID NO:10) and 5'-GATCGTCGACTCGA-3' (SEQ ID NO:11) were annealed and ligated into the single Bam HI site to generate pZIPneo$_{Sal}$. The erbB-3 open reading frame including 7 nucleotides upstream of the initiation codon and the termination codon (nucleotides 93–4128) was linkered with Sal I ends, employing the polymerase chain reaction (PCR) and cloned into pZIPneo$_{Sal}$(LTR-erbB). Sense orientation and integrity of the open reading frame were confirmed by restriction analysis as well as nucleotide sequence analysis of cloning boundaries and PCR-amplified regions.

For structural and functional characterization of the erbB-3 gene product, the complete erbB-3 open reading-frame was inserted as given above into the modified ZIPneo vector, placing the cDNA under the transcriptional control of the Moloney murine leukemia virus long-terminal-repeat sequence (LTR-erbB-3). NIH/3T3 fibroblasts were transfected with LTR-erbB-3 or LTR-neo control DNA and cultured in the presence or absence of the selective drug G418. Under conditions in which efficient drug resistance (6×10$^3$ colonies/pmol) was conferred by LTR-erbB-3, no transformed foci were detectable. In contrast, LTR-erbB-2 or EGF-triggered LTR-EGFR induced morphological transformation of NIH-3T3 cells with efficiencies of around 1.2×10$^4$/pmol and 2.3×10$^2$/pmol, respectively.

Figure 8A:
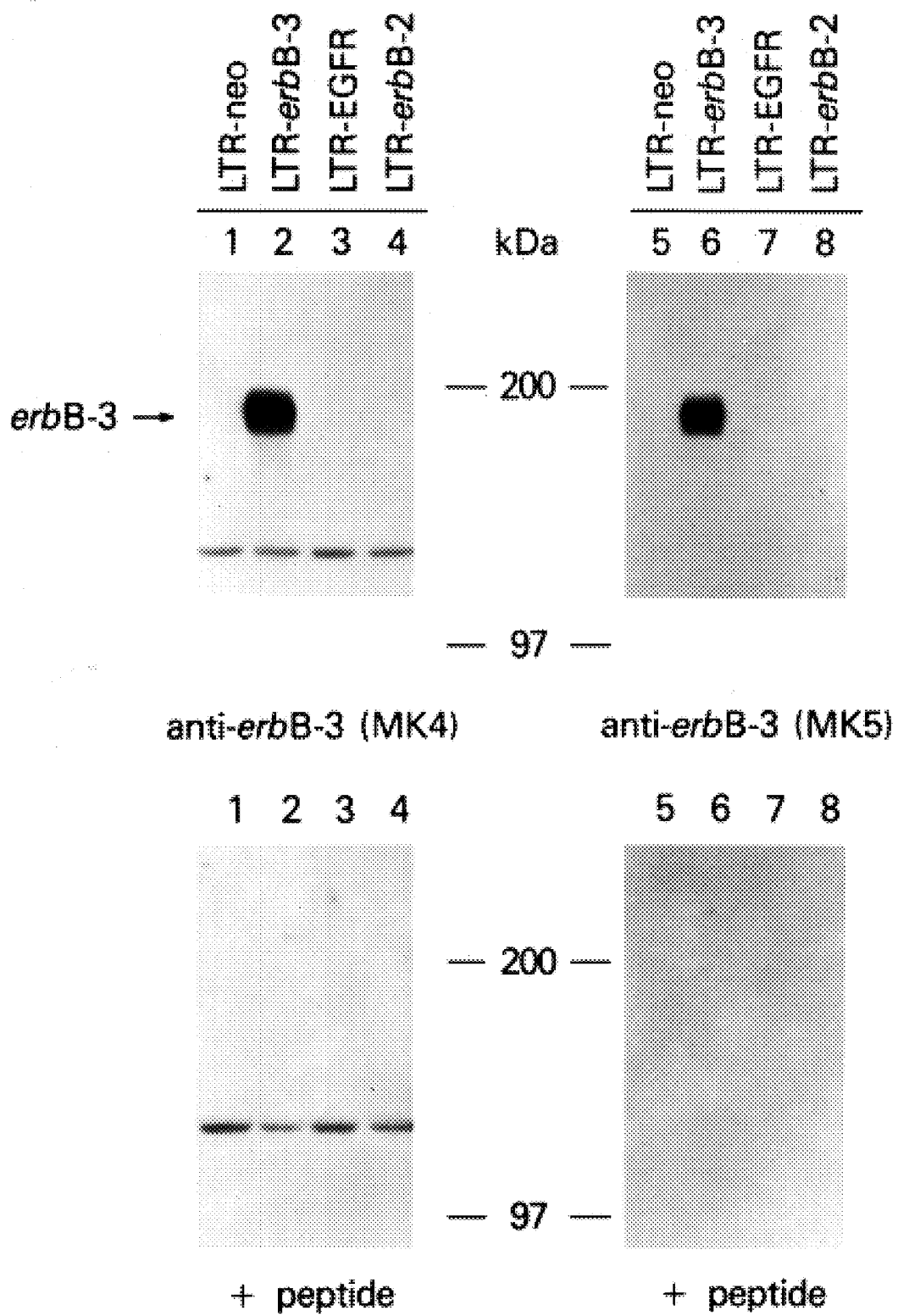

To test for expression of the erbB-3 protein, polyclonal rabbit antisera, including MK4 and MK5, were developed against synthetic peptides. MK4 and MK5 were raised against peptides that encompass the residues given in SEQ ID NO:5 and SEQ ID NO:6, respectively, which are within the carboxyl terminus of the predicted erbB-3 product. For immunization, peptides were coupled to thyroglobulin using glutaraldehyde. Immunoblot analysis of lysates from marker-selected LTR-neo and LTR-erbB-3 transfectants revealed a major 180 kDa band only in LTR-erbB-3 cells. This band was independently recognized by both antisera (FIG. 8A). There was no cross-reactivity of either antiserum with the related EGFR or erbB-2 proteins overexpressed in NIH/3T3 cells. Immunoreactivity of either antiserum with the 180 kDa band in LTR-erbB-3 transfectants was competed by the antigenic peptide, while MK4 reactivity with a faint 125 kDa band was not affected by preincubation with peptide (FIG. 8A). These results established specificity of erbB-3 protein detection by both polyclonal antisera. By comparison, the 180 kDa erbB-3 protein migrated distinctly slower than the 170 kDa EGFR and slightly faster than the 185 kDa erbB-2 protein.

To characterize processing of the erbB-3 protein, we performed immunoprecipitation experiments with MK5 antiserum. Metabolic labeling of LTR-erbB-3 transfectants in the presence or absence of tunicamycin demonstrated that the 145 kDa erbB-3 core polypeptide is modified by N-linked glycosylation (FIG. 8B). Pulse-chase analysis further indicated cotranslational processing, resulting in a predominant 170 kDa precursor protein in addition to faint erbB-3 specific bands of 150 kDa and 160 kDa, following 15 min of pulse-labeling (FIG. 8C). The mature 180 kDa erbB-3 protein appeared after 0.5 h of chase, and the majority was converted into gp180$^{erbB-3}$ by 1 h. By analysis of further time points, we estimate an approximate half-life of 2–3 h (FIG. 8C). Thus, in NIH/3T3 cells, gp180$^{erbB-3}$ exhibits an apparently faster turn-over than the EGFR, for which a biosynthesis time of 3h and approximate half-life of 3–6 h has been reported.

Figure 9A:
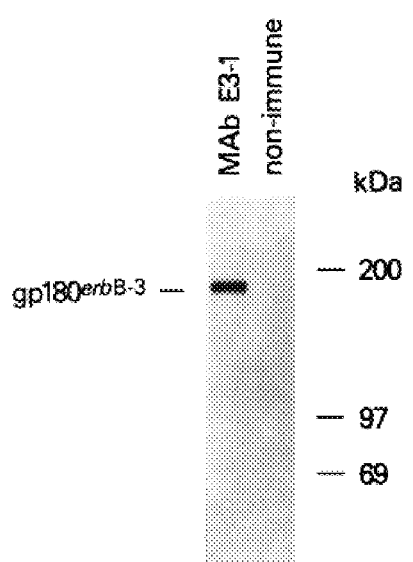
FIGS. 9A, 9B, 9C and 9D. Immunolocalization of gp180$^{erbB-3}$ on the surface of LTR-erbB-3 cells.
Figure 9B:
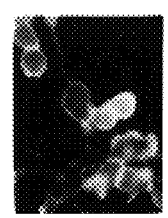
Figure 9D:
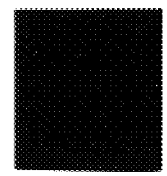
Figure 9C:
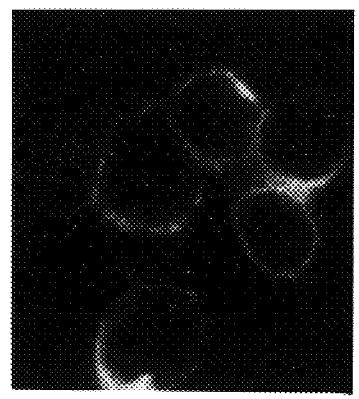

For immunolocalization of the erbB-3 protein, erbB-3-specific monoclonal antibodies, including MAb E3-1, were raised against the recombinantly expressed protein. BALB/c mice were immunized with live LTR-erbB-3 cells. Somatic cell hybrids were prepared by fusion of immune splenocytes with murine non-secreting myeloma cells NS-1. Hybridoma supernatants were screened for differential immunoreactivity with LTR-erbB-3 but not LTR-neo transfectants by enzyme-linked immunosorbent assay (ELISA) using both live cells or cell extracts as antigen source. Positive hybridoma cell lines were cloned twice by limiting dilution and further characterized by immunoprecipitation and immunofluorescence analysis. One monoclonal antibody; MAb E3-1 (IgG2a isotype), specifically immunoprecipitated gp180$^{erbB-3}$ from LTR-erbB-3 transfectants (FIG. 9A) and did not exhibit cross-reactivity with the EGFR or erbB-2 proteins overexpressed in an NIH/3T3 cell background. Immunofluorescence analysis using a labeled second antibody revealed heterogeneous membrane immunostaining of formalin-fixed LTR-erbB-3 cells using MAb E3-1, but not with a non-specific immunoglobulin of matching isotype (FIG. 9B). MAb E3-1-specific membrane fluorescence of native LTR-erbB-3 cells (FIG. 9B) indicated that gp180$^{erbB-3}$ was expressed at the cell surface, as expected for a membrane-anchored protein.

Figure 10A:
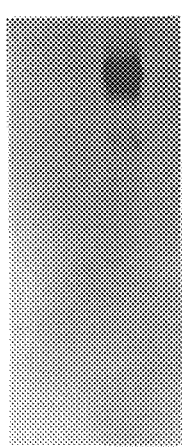
FIGS. 10A, 10B, and 10C. Autophosphorylation in vitro and chronic tyrosine phosphorylation in vivo of gp180$^{erbB-3}$. LTR-erbB-3 or control lysates were immunoprecipitated with erbB-3 monoclonal antibody (E3-1) or non-immune IgG (NI). Parallel immunoprecipitates were subjected either to immunoblot analysis with MK4 antiserum (FIG. 10A) or to an immunocomplex kinase assay in the presence of [$^{32}$P]-γATP (FIG. 10B). Tyrosine Phosphorylation in vivo was assayed by immunoprecipitation with monoclonal anti-P-Tyr antibodies followed by immunoblotting with MK4 antiserum (FIG. 10C)
Figure 10B:
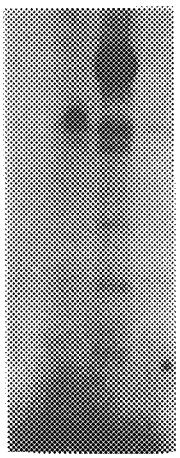
Figure 10C:
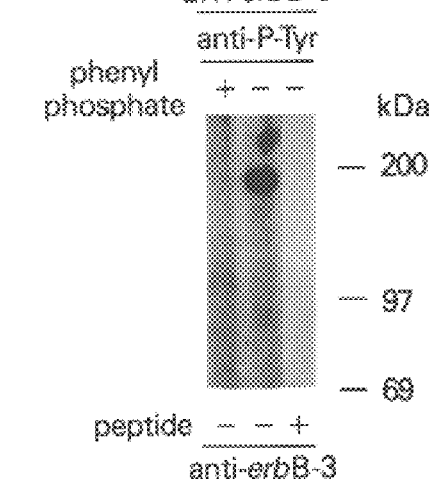

To investigate its function, we next analyzed the erbB-3 protein for in vitro kinase activity. LTR-erbB-3 and control LTR-neo cell lysates were first immunoprecipitated with E3-1 followed by immunoblot analysis with MK4 antiserum (FIG. 10A). When the same immunoprecipitates were incubated in autokinase buffer containing [$^{32}$P]-γATP, a predominant 180 kDa phosphoprotein was labeled only in immunoprecipitates containing the erbB-3 protein (FIG. 10B). These findings indicated that gp180$^{erbB-3}$ possessed intrinsic protein kinase activity. To assess its enzymatic activity in vivo, LTR-erbB-3 lysates wore subjected to immunoprecipitation with phosphotyrosine-specific monoclonal antibodies (anti-P-Tyr) followed by immunoblotting with MK4 antiserum. As shown in FIG. 10C, the erbB-3 protein was recovered from anti-P-Tyr immunoprecipitates, and immunodetection was competed either by phenyl phosphate in the immunoprecipitation or the erbB-3 peptide in Western blot analysis. These findings indicated that recombinant gp180$^{erbB-3}$ expressed in NIH/3T3 cells was chronically phosphorylated on tyrosine residues.

The protein lysates were prepared in Staph A buffer containing the protease inhibitors phenylmethyl sulfonyl fluoride (1 mM) and aprotinin (10 μg/ml; Boehringer Mannheim). For the analysis of phospho-tyrosine proteins, the phosphatase inhibitors sodium orthovanadate (2 mM) and sodium pyrophosphate (10 mM) were added. Immunoblot analysis using peptide antisera was essentially conducted as previously reported. For the detection of phosphotyrosine proteins, membranes were blocked in PBS containing 5% BSA and immunostained with a mixture of monoclonal anti-P-Tyr antibodies (PY20 and PY69; ICN) diluted 1:500 in PBS containing 1% BSA. Filters were washed with PBS containing 0.05% Tween20. Immunoprecipitation was conducted using gammabind G agarose (Pharmacia) to collect the immunocomplexes. The beads were coupled with goat anti-mouse-IgG second antibody (Boehringer Mannheim) in immunoprecipitations using erbB-3 or EGFR monoclonal antibodies. For in vitro kinase assays, 4 mg total lysates were precleared with gammabind G agarose. Following immunoprecipitation, washed immunocomplexes were equilibrated in autokinase buffer containing 40 mM Hepes 7.5, 10 mM $MgCl_2$, and 0.05% Triton. The immunocomplexes were subsequently divided for immunoblot analysis or immunocomplex kinase assay, respectively. Autokinase reactions were carried out in 40 $\mu$l autokinase buffer containing 20 Ci $\gamma$ATP (3000 ci/mmol) at 25° for 10 min and terminated by addition of SDS containing sample buffer.

EXAMPLE 7

EGF-dependent mitogenic signaling by an EGFR/ erb B-3 chimeric receptor

To explore erbB-3 signaling, a chimeric receptor, LTR-EGFR/erbB-3, containing the ligand-binding domain of the closely related EGF receptor (aa 1–682) and the intracellular portion of erbB-3 (aa 681–1342) was engineered. Linearized expression constructs (0.01–10 $\mu$g/plate) were transfected into NIH/3T3 cells by calcium phosphate precipitation using 40 $\mu$g of calf thymus DNA as carrier. Mass cultures expressing the recombinant proteins were obtained by selection with 750 $\mu$g/ml G418. Selected LTR-EGFR/erbB-3 transfectants were enriched for expression of the chimeric protein by preparative FACS sorting using EGFR monoclonal antibody AB-1 (Oncogene Sciences).

Transfection of NIH/3T3 cells with this construct did not result in detectable focus formation either in the presence or absence of EGF. To quantitate expression of the chimeric receptor, selected mass cultures were analyzed for EGF-binding in comparison to NIH/3T3 cells overexpressing the EGFR (LTR-EGFR). Scatchard analysis established around $5.7 \times 10^5$ EGF binding sites/cell for the LTR-EGFR/erbB-3 transfectant as compared to $2.5 \times 10^6$ binding sites/cell for LTR-EGFR transfectant. The LTR-EGFR/erbB-3 transfectant exhibited two populations of binding sites with affinities of 0.11 nM and 5 nM, respectively. The high-affinity sites were in the minority ($2.3 \times 10^4$), and there were $5.5 \times 10^5$ low-affinity binding sites. Similar results were obtained with the wild-type EGFR in LTR-EGFR transfectants, which displayed $1.1 \times 10^5$ high affinity (0.13 nM) and $2.4 \times 10^6$ low affinity receptors (7 nM).

Figure 11:
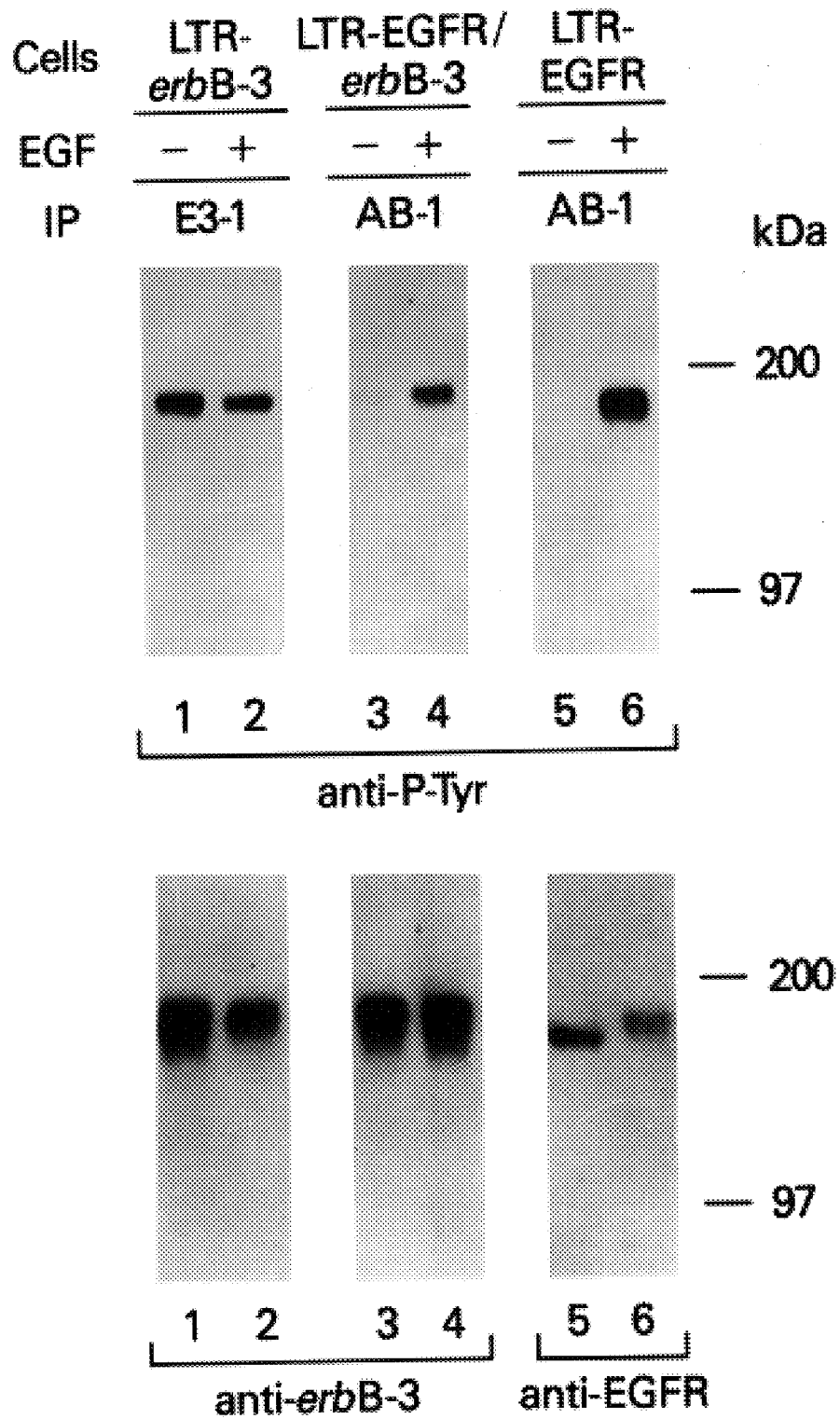
FIG. 11. EGF-dependent tyrosine phosphorylation of an EGFR/erbB-3 chimeric receptor, gp180$^{EGFR/erbB-3}$. Serum-starved LTR-erbB-3, LTR-EGFR/erbB-3, and LTR-EGFR transfectants were triggered with 100 ng/ml EGF. Similar amounts of gp180$^{erbB-3}$, gp180$^{EGFR/erbB-3}$, and EGFR were immunoprecipitated with erbB-3 (E3-1) or EGFR (AB-1) monoclonal antibodies followed by immunoblot analysis with anti-P-Tyr antibodies or peptide antisera.

To investigate EGF responsiveness of erbB-3 enzymatic activity, the in vivo tyrosine phosphorylation of the chimeric receptor in the presence or absence of EGF was compared. This protein, as well as the EGFR and erbB-3 proteins from independent transfectants, was enriched by immunoprecipitation and subjected to immunoblot analysis with either anti-P-Tyr or the appropriate specific antiserum. As shown in FIG. 11, the steady state level of tyrosine phosphorylated gp180$^{erbB-3}$ in NIH/3T3 cells was not altered upon EGF exposure (lane 1,2). The chimeric EGFR/erbB-3 receptor, which was expressed as a 180 kDa protein, gp180$^{EGFR/erbB-3}$ displayed low, but detectable level of tyrosine phosphorylation in scrum-free medium (lane 3). However, EGF triggering of the chimera resulted in a substantial increase in tyrosine phosphorylation, demonstrating EGF-dependent activation of erbB-3 catalytic function (lane 4). The wild-type EGFR showed somewhat higher level of EGF-dependent tyrosine phosphorylation under the same conditions (lane 6). Of note, the relative level of gp180$^{erbB-3}$ tyrosine phosphorylation was comparable to that of EGF-activated chimeric receptor expressed at a similar protein level, indicating constitutive activation of erbB-3 catalytic properties in LTR-erbB-3 transfectants.

Whether the erbB-3 catalytic domain was capable of transducing a mitogenic signal was then assessed. When the LTR-EGFR/erbB-3 transfectant was exposed to increasing EGF concentrations, there was a dose-dependent stimulation of DNA synthesis similar to that observed with EGFR overexpressing NIH-3T3 cells. Under the same conditions, neither LTR-neo nor LTR-erbB-3 transfectants showed a significant increase in DNA synthesis even at high EGF concentrations, consistent with previous observations. It should be noted that basal levels of DNA synthesis of the LTR-erbB-3 transfectant were 2–3 fold above those of the other transfactants, findings that were reproducible with several independent selected mass cultures.

The biological effects of activated erbB-3 catalytic function were assessed by testing the transfectants for anchorage-independent growth. To test anchorage-independent growth, cell suspensions were seeded at 10-fold serial dilutions in semisolid agarose medium containing growth medium and 0.45% seaplaque agarose (FMC Corp.). Visible colonies comprising >100 cells were scored at 14 days. EGF was added at a concentration of 20 ng/ml. Human mammary tumor cell lines were obtained from the American Type Culture Collection and propagated in Dulbecco's modified Eagle medium containing 10% fetal calf serum.

As shown in Table 2, LTR-neo transfectants failed to exhibit significant soft agar growth in the presence or absence of EGF. In contrast, EGF induced soft agar colony formation with both LTR-EGFR/erbB-3 and LTR-EGFR transfectants. The latter showed a larger colony number (Table 2) as well as colony size (data not shown). By comparison, the LTR-erbB-3 transfectant displayed EGF-independent colony formation with an efficiency similar to that of EGF-activated LTR-EGFR/erbB-3 transfectant (Table 2). All of these findings establish that ligand activation of a chimeric EGFR/erbB-3 receptor causes mitogenic signaling in NIH/3T3 cells and suggest that chronic tyrosine phosphorylation of erbB-3 in LTR-erbB-3 transfectants is associated with constitutive signaling in these cells.

TABLE 2

Anchorage-independent growth of NIH/3T3 transfectants

| NIH3T3 transfectants | #colonies*/$10^4$ cells | |
|---|---|---|
|  | −EGF | +EGF |
| LTR-neo | 1 (±1) | 4 (±2) |
| LTR-EGFR | 2 (±2) | 206 (±49) |
| LTR-EGFR/erbB-3 | 7 (±3) | 88 (±16) |
| LTR-erbB-3 | 97 (±20) | 94 (±29) |

*mean (± standard error) of 3 independent assays

EXAMPLE 8

Evidence for activated erbB-3 signaling function in human breast tumor cells

Figure 12:
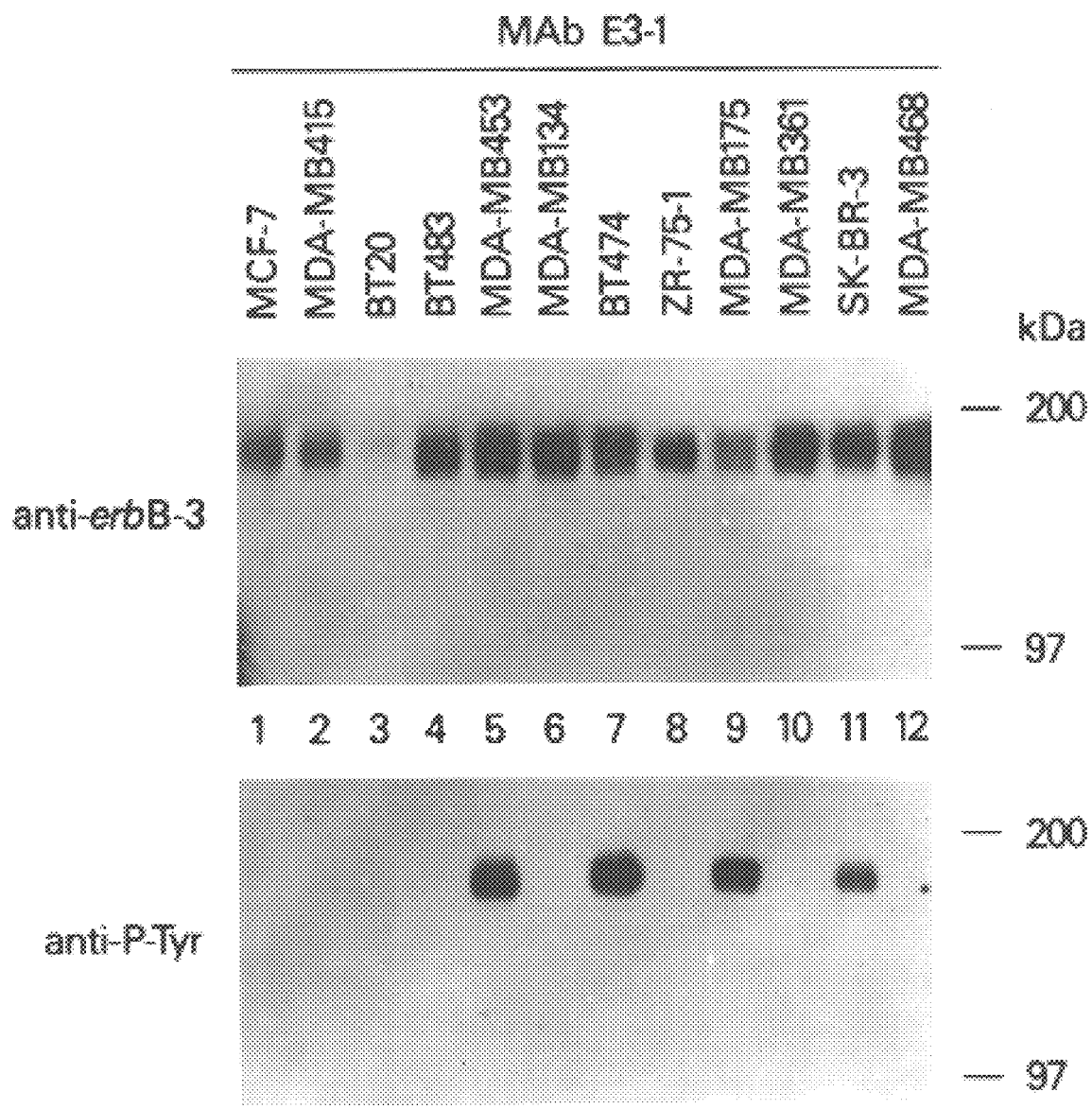
FIG. 12. Activation of gp180$^{erbB-3}$ signaling function in human breast tumor cells. The erbB-3 protein was immunoprecipitated with MAb E3-1 from 1 mg total protein lysate and subjected to immunoblot analysis with erbB-3 peptide antiserum or phosphotyrosine antibodies as indicated.

The availability of erbB-3 specific antibodies made it possible to explore expression and activity of gp180$^{erbB-3}$ in human tumor cells. Based upon our previous evidence for erbB-3 mRNA overexpression in certain breast cancer cell lines, we measured erbB-3 protein levels and tyrosine phosphorylation in such tumor lines, using the procedures given above. Following immunoprecipitation with Mab E3-1, immunoblot analysis with MK4 antiserum revealed the natural human erbB-3 product as a 180 kDa protein. The levels of erbB-3 protein varied markedly along the tumor lines analyzed, with highest expression in BT483, MDA-MB453, MDA-MB134, MDA-MB361, SK-BR-3, and MDA-MB468 (FIG. 12). The lowest levels were observed in BT20 and MDA-MB175 cell lines (FIG. 12), comparable with that expressed by nonmalignant 184B5 mammary epithelial cells (data not shown). Thus, erbB-3 protein expression varied by at least 20–30 fold among the lines tested, consistent with results of transcript analysis (data not shown).

Immunoblot analysis of the same immunoprecipitates with anti-P-Tyr antibodies revealed that tyrosine phosphorylation of the native erbB-3 product was undetectable in 8 of the tumor cell lines, including MDA-MB134, MDA-MB361, and MDA-MB468, which harbored increased erbB-3 levels. In contrast, erbB-3 protein expressed by 4 cell lines, including MDA-MB453, BT474, MDA-MB175, and SK-BR-3, demonstrated readily detectable chronic tyrosine phosphorylation (FIG. 12, lanes 5, 7, 9 and 11). In MDA-MB175, there was no significantly elevated level of erbB-3 protein. Thus, in 4 out of 12 breast tumor cell lines, the $gp180^{erbB-3}$ signaling function was activated at steady state. Whether chronic erbB-3 phosphorylation involves autocrine stimulation or subtle structural alterations, these findings provide evidence for constitutive $gp180^{erbB-3}$ activation in these human breast tumor cells.

EXAMPLE 9

Identification, purification and characterization of erbB-3 ligands

As shown in FIG. 12, the $gp180^{erbB-3}$ that is overexpressed in some human breast tumor cell lines can be either functionally activated or not, depending on the cell line. Further, in some other human breast tumor cell lines, the erbB-3 polypeptide is not overexpressed and, again, can be either activated or not activated. These differences, and the common property of growth factor receptor-like tyrosine kinases to rapidly autophosphorylate on tyrosine residues in response to ligand triggering, can be exploited to identify, isolate and characterize ligands, preferably specific ligands, that can activate or down-regulate erbB-3. The term "erbB-3 ligand" refers to a molecule that binds to the erbB-3 protein, particularly to the extracellular domain of the erbB-3 protein, and can activate ("erbB-3 activating ligand") or down-regulate ("erbB-3 blocking ligand") the biochemical and/or biological activity of the erbB-3 protein. Depending on the concentration of the ligand, a ligand can both activate and down-regulate activity.

A source containing a potential erbB-3 ligand, such as conditioned medium, body fluid extracts, cell extracts, tissue extracts or the like, with or without agents which can modify erbB-3 activity, can be screened for the presence of such a ligand by the ability of the solution, in the case of an activating ligand, to enhance erbB-3 phosphorylation. With respect to screening for an erbB-3 activating ligand, cells from a cell line whose expressed erbB-3 protein contains nonexistent or low level intrinsic tyrosine phosphorylation can be contacted with potential ligand sources or control medium for a time and under conditions sufficient to allow binding of an erbB-3 ligand, if present, to bind to erbB-3. Typically, if an erbB-3 ligand is present, binding will occur within a short time. Thus, the cells are exposed to potential ligand sources or control medium for, preferably, no longer than 30 minutes, most preferably, 10 minutes or less. Appropriate conditions to allow binding of the ligand can be determined by one skilled in the art, such as physiological conditions at 37° C. or the conditions given in FIG. 5 of Holmes et al., Science 256:1205 (1992). erbB-3 modifying agents, if administered, can be present in a concentration between $10^{-2}$ pM and $10^5$ pM. The cell line employed can overexpress erbB-3, such as the mammary tumor cell lines MDA-MB415, MDA-MB134, MDA-MB468, BT483, MDA-MB361, MCF-7 and ZR-75-1, which express an increased amount of the erbB-3 protein with low level intrinsic tyrosine phosphorylation compared to protein amounts and activation levels for corresponding nonmalignant cells. One such potential activating ligand source can be derived from cell lines that not only overexpress erbB-3 but also exhibit high level intrinsic tyrosine phosphorylation, such as MDA-MB453, SK-BR-3, and BT474. In addition, any normal cell which does not overexpress erbB-3 can be utilized, e.g., fibroblasts.

Similarly, with respect to screening for an erbB-3 inhibitory down-regulating ligand, a cell line whose expressed erbB-3 protein contains high level intrinsic tyrosine phosphorylation can be exposed to potential ligand sources or control medium for a time and under conditions sufficient to allow binding of an erbB-3 ligand, if present, to bind to erbB-3. The cell line employed preferably expresses activated erbB-3, such as the mammary tumor cell lines MDA-MB453, SK-BR-3 and BT474. In addition, an activating ligand at higher concentration can be down-regulating. Such activity can be routinely screened given the teaching herein.

The triggering or blocking of erbB-3 activation can be detected by comparing the level of erbB-3 tyrosine phosphorylation in the cell line after exposure to the potential ligand source with the normal level, e.g., the level obtained after exposure to the control medium. For example, in a negative control the cells can be in serum free medium and for activating ligand the conditioned medium is from cell lines with increased erbB-3 that don't have phosphorylation. For instance, to measure erbB-3 specific tyrosine phosphorylation, potentially triggered (or blocked) cells and the control cells are lysed. Using procedures such as those discussed above, the erbB-3 protein is immunoprecipitated with an erbB-3 specific antibody, preferably a monoclonal such as MAb E3-1. The immunoprecipitates are divided and subjected to immunoblot analysis with either antiphosphotyrosine or erbB-3 antibodies. The presence of an erbB-3 activating or blocking ligand can be monitored by a relative increase or decrease, respectively, of phosphotyrosine levels in comparison to the untriggered control. Any increase can be significant, especially a two-fold or greater increase. This ligand-detection system can be used repeatedly throughout the ligand purification procedures so as to monitor protein purification of the erbB-3 ligand to homogeneity.

Alternatively, following exposure of the cell lines to the potential ligand source as discussed above, detection of an erbB-3 activating ligand or blocking ligand can be accomplished by measurement of cell growth and/or mitogenic signals resulting from the activation or inhibition of erbB-3 catalytic activity, using, for example, the procedures given in Example 7 above. An increase in colony number or colony size and/or a dose-dependent increase of DNA synthesis for the cells exposed to the potential ligand relative to those exposed to the control medium correlates with the presence of an activating ligand in the potential ligand source. Conversely, respective decreases correlate with the presence of a blocking ligand in the potential ligand source.

Following the isolation and purification of the erbB-3 ligand, the identity of the ligand can be determined by protein identification methods known in the art, such as amino acid sequencing. Further, the erbB-3 ligand can be molecularly characterized. For instance, similar to the procedures outlined in Holmes et al., *Science* 256:1205 (1992), the nucleic acid sequence that corresponds to the ligand's amino acid sequence, or a partial amino acid sequence corresponding to a portion of the ligand, can be used to design degenerate oligonucleotide probes corresponding to the amino acid sequence or partial sequence. These degenerate oligonucleotides can be used to screen a cDNA library and generate a clone that encodes the precursor of the erbB-3 ligand. Following determination of the coding sequence, related coding sequences can be discovered by screening other libraries.

For purposes of completing the background description and present disclosure, each of the published articles, patents and patent applications heretofore identified in this specification are hereby incorporated by reference into the specification.

The foregoing invention has been described in some detail for purposes of clarity and understanding. It will also be obvious that various changes and combinations in form and detail can be made without departing from the scope of the invention.

SEQUENCE LISTING

```
(1) GENERAL INFORMATION:

(iii) NUMBER OF SEQUENCES: 12

(2) INFORMATION FOR SEQ ID NO:1:

(i) SEQUENCE CHARACTERISTICS:
        (A) LENGTH: 1542 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: exon
        (B) LOCATION: 66..221

(ix) FEATURE:
        (A) NAME/KEY: exon
        (B) LOCATION: 780..855

(ix) FEATURE:
        (A) NAME/KEY: exon
        (B) LOCATION: 1040..1185

(ix) FEATURE:
        (A) NAME/KEY: intron
        (B) LOCATION: 222..779

(ix) FEATURE:
        (A) NAME/KEY: intron
        (B) LOCATION: 856..1039

(ix) FEATURE:
        (A) NAME/KEY: CDS
        (B) LOCATION: join(66..221, 780..855, 1040..1185)

(xi) SEQUENCE DESCRIPTION: SEQ ID NO:1:

GAATTCCAGA TCTCAGTGAC TGATTCCCCC AACCTTAAGA ATACTTTCTT CCCCTATACC      60

TACAG GGA ATG TAC TAC CTT GAG GAA CAT GGT ATG GTG CAT AGA AAC        107
      Gly Met Tyr Tyr Leu Glu Glu His Gly Met Val His Arg Asn
        1               5                  10

CTG GCT GCC CGA AAC GTG CTA CTC AAG TCA CCC AGT CAG GTT CAG GTG      155
Leu Ala Ala Arg Asn Val Leu Leu Lys Ser Pro Ser Gln Val Gln Val
 15                  20                  25                  30

GCA GAT TTT GGT GTG GCT GAC CTG CTG CCT CCT GAT GAT AAG CAG CTG      203
Ala Asp Phe Gly Val Ala Asp Leu Leu Pro Pro Asp Asp Lys Gln Leu
                     35                  40                  45

CTA TAC AGT GAG GCC AAG GTGAGGAGAC ACAAAGGGTA AGGAGGCGGG             251
Leu Tyr Ser Glu Ala Lys
```

```
                50
GGTGGAGTGA AGCATGGGGA TAGGGAGCAG CCAGTGGTCT CTTCCAGAGG CAAGCAGATG        311

CTTCATGGTA AGTTCAAGGA GAGAAGGCTG CAGATGCCAG ATATTTTAGT TCAGAGGGCA        371

ACAAAGAAAA TAATGATCAA GAACTTGGGA CTGGCCGGGC GCGGTGGCTC ACGCCTGTAA        431

TCCCAACACT TCGGGAGGCC AAGGCGGGTG GATCACAAGG TCAGGAGATC AAGACCATCC        491

TGGCTAGCAC GGTGAAACCC CGTCTCTACT AAATATACAA AAAAAAAAAA ATTAGCCAGG        551

CGTGGCGGCA TGCATCTGTA CTCCCAGCTA CTCGGGAGGC TGAGGCAGGA GAATGGCGTG        611

AACCCAGGAG GCGGAGCTTG CAGTGGGCCG AGATCGCACC ACTGCACTCC AGTCTGGGCG        671

ACAGAGCGAG ACTCCGTCTC AAAAAAAAAA AAAAAAGAAT TTGGGACTTG GAAATCCTAA        731

GAAAATTTGT GGAAATAAAC TTGTGATACC TCTATCTTTA ATCCGCAG ACT CCA ATT        788
                                                    Thr Pro Ile
                                                             55

AAG TGG ATG GCC CTT GAG AGT ATC CAC TTT GGG AAA TAC ACA CAC CAG        836
Lys Trp Met Ala Leu Glu Ser Ile His Phe Gly Lys Tyr Thr His Gln
             60                  65                  70

AGT GAT GTC TGG AGC TAT  G GTCAGTGCAT CTGGATGCCC TCTCTACCAT            885
Ser Asp Val Trp Ser Tyr
             75

CACTGGCCCC AGTTTCAAAT TTACCTTTTG AGAGCCCCCT CTTAGAATCT CTAAGCACTT        945

CAGATTTTTG TGTTAGATCA GGTTCTGCCT TCCCTTCACT TCATGCCCAT GTCTACTATT       1005

TTGCCAGTGA CTAGTCCATG TCTTCCTGCA ACAG  GT GTG ACA GTT TGG GAG          1056
                                      Gly Val Thr Val Trp Glu
                                                         80

TTG ATG ACC TTC GGG GCA GAG CCC TAT GCA GGG CTA CGA TTG GCT GAA       1104
Leu Met Thr Phe Gly Ala Glu Pro Tyr Ala Gly Leu Arg Leu Ala Glu
 85                  90                  95

GTA CCA GAC CTG CTA GAG AAG GGG GAG CGG TTG GCA CAG CCC CAG ATC       1152
Val Pro Asp Leu Leu Glu Lys Gly Glu Arg Leu Ala Gln Pro Gln Ile
100                 105                 110                 115

TGC ACA ATT GAT GTC TAC ATG GTG ATG GTC AAG TGTGAGTTAC CTGCTGAGCC     1205
Cys Thr Ile Asp Val Tyr Met Val Met Val Lys
                    120                 125

CAACCATTTT CTCTTTTTTT CTTTTTTTTT CTTTTTTTTT TTTTTTTGAG ACAGAGTCTC      1265

ACAATTGTCA CCCAGGCTGG AGTGCAATGG TGCAATCAAT CTTGGCTCAC TACAACCTCC      1325

GCCTCTCGGG TTCAAGAGAT TCTCCTGCTT CAGCTCCGGA GTAGCTGGGA TTACAGCGCC      1385

CGCCACACCT GGATAACTGT TACACTTTTA GTAGAGATGG GGTTTCACCA TGTTGGCCAG      1445

GCTGGTCTCA AACTCCTGAC CTCAGGTGAT CCGCCTGCCT CAGCTTCCCA AAGTGCTGGG      1505

ATTACAGGTG TGAGCCATCA TGCTCGCCTG ACTGCAG                              1542

(2) INFORMATION FOR SEQ ID NO:2:

(i) SEQUENCE CHARACTERISTICS:
        (A) LENGTH: 126 amino acids
        (B) TYPE: amino acid
        (D) TOPOLOGY: linear (ii) MOLECULE TYPE: protein (xi) SEQUENCE DESCRIPTION: SEQ ID NO:2:

Gly Met Tyr Tyr Leu Glu Glu His Gly Met Val His Arg Asn Leu Ala
 1               5                  10                  15
```

```
Ala Arg Asn Val Leu Leu Lys Ser Pro Ser Gln Val Gln Val Ala Asp
         20                  25                  30

Phe Gly Val Ala Asp Leu Leu Pro Pro Asp Asp Lys Gln Leu Leu Tyr
     35                  40                  45

Ser Glu Ala Lys Thr Pro Ile Lys Trp Met Ala Leu Glu Ser Ile His
 50                  55                  60

Phe Gly Lys Tyr Thr His Gln Ser Asp Val Trp Ser Tyr Gly Val Thr
 65                  70                  75                  80

Val Trp Glu Leu Met Thr Phe Gly Ala Glu Pro Tyr Ala Gly Leu Arg
                 85                  90                  95

Leu Ala Glu Val Pro Asp Leu Leu Glu Lys Gly Glu Arg Leu Ala Gln
             100                 105                 110

Pro Gln Ile Cys Thr Ile Asp Val Tyr Met Val Met Val Lys
         115                 120                 125

(2) INFORMATION FOR SEQ ID NO:3:

(i) SEQUENCE CHARACTERISTICS:
        (A) LENGTH: 4905 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 100..4125

(xi) SEQUENCE DESCRIPTION: SEQ ID NO:3:

ACCAATTCGC CAGCGGTTCA GGTGGCTCTT GCCTCGATGT CCTAGCCTAG GGGCCCCCGG      60

GCCGGACTTG GCTGGGCTCC CTTCACCCTC TGCGGAGTC ATG AGG GCG AAC GAC       114
                                            Met Arg Ala Asn Asp
                                             1               5

GCT CTG CAG GTG CTG GGC TTG CTT TTC AGC CTG GCC CGG GGC TCC GAG     162
Ala Leu Gln Val Leu Gly Leu Leu Phe Ser Leu Ala Arg Gly Ser Glu
                 10                  15                  20

GTG GGC AAC TCT CAG GCA GTG TGT CCT GGG ACT CTG AAT GGC CTG AGT     210
Val Gly Asn Ser Gln Ala Val Cys Pro Gly Thr Leu Asn Gly Leu Ser
             25                  30                  35

GTG ACC GGC GAT GCT GAG AAC CAA TAC CAG ACA CTG TAC AAG CTC TAC     258
Val Thr Gly Asp Ala Glu Asn Gln Tyr Gln Thr Leu Tyr Lys Leu Tyr
         40                  45                  50

GAG AGG TGT GAG GTG GTG ATG GGG AAC CTT GAG ATT GTG CTC ACG GGA     306
Glu Arg Cys Glu Val Val Met Gly Asn Leu Glu Ile Val Leu Thr Gly
     55                  60                  65

CAC AAT GCC GAC CTC TCC TTC CTG CAG TGG ATT CGA GAA GTG ACA GGC     354
His Asn Ala Asp Leu Ser Phe Leu Gln Trp Ile Arg Glu Val Thr Gly
 70                  75                  80                  85

TAT GTC CTC GTG GCC ATG AAT GAA TTC TCT ACT CTA CCA TTG CCC AAC     402
Tyr Val Leu Val Ala Met Asn Glu Phe Ser Thr Leu Pro Leu Pro Asn
                 90                  95                 100

CTC CGC GTG GTG CGA GGG ACC CAG GTC TAC GAT GGG AAG TTT GCC ATC     450
Leu Arg Val Val Arg Gly Thr Gln Val Tyr Asp Gly Lys Phe Ala Ile
             105                 110                 115

TTC GTC ATG TTG AAC TAT AAC ACC AAC TCC AGC CAC GCT CTG CGC CAG     498
Phe Val Met Leu Asn Tyr Asn Thr Asn Ser Ser His Ala Leu Arg Gln
         120                 125                 130

CTC CGC TTG ACT CAG CTC ACC GAG ATT CTG TCA GGG GGT GTT TAT ATT     546
Leu Arg Leu Thr Gln Leu Thr Glu Ile Leu Ser Gly Gly Val Tyr Ile
     135                 140                 145
```

-continued

| | | |
|---|---|---|
| GAG AAG AAC GAT AAG CTT TGT CAC ATG GAC ACA ATT GAC TGG AGG GAC<br>Glu Lys Asn Asp Lys Leu Cys His Met Asp Thr Ile Asp Trp Arg Asp<br>150                                155                                160                                165 | 594 |

```
GAG AAG AAC GAT AAG CTT TGT CAC ATG GAC ACA ATT GAC TGG AGG GAC    594
Glu Lys Asn Asp Lys Leu Cys His Met Asp Thr Ile Asp Trp Arg Asp
150                 155                 160                 165

ATC GTG AGG GAC CGA GAT GCT GAG ATA GTG GTG AAG GAC AAT GGC AGA    642
Ile Val Arg Asp Arg Asp Ala Glu Ile Val Val Lys Asp Asn Gly Arg
                170                 175                 180

AGC TGT CCC CCC TGT CAT GAG GTT TGC AAG GGG CGA TGC TGG GGT CCT    690
Ser Cys Pro Pro Cys His Glu Val Cys Lys Gly Arg Cys Trp Gly Pro
            185                 190                 195

GGA TCA GAA GAC TGC CAG ACA TTG ACC AAG ACC ATC TGT GCT CCT CAG    738
Gly Ser Glu Asp Cys Gln Thr Leu Thr Lys Thr Ile Cys Ala Pro Gln
        200                 205                 210

TGT AAT GGT CAC TGC TTT GGG CCC AAC CCC AAC CAG TGC TGC CAT GAT    786
Cys Asn Gly His Cys Phe Gly Pro Asn Pro Asn Gln Cys Cys His Asp
    215                 220                 225

GAG TGT GCC GGG GGC TGC TCA GGC CCT CAG GAC ACA GAC TGC TTT GCC    834
Glu Cys Ala Gly Gly Cys Ser Gly Pro Gln Asp Thr Asp Cys Phe Ala
230                 235                 240                 245

TGC CGG CAC TTC AAT GAC AGT GGA GCC TGT GTA CCT CGC TGT CCA CAG    882
Cys Arg His Phe Asn Asp Ser Gly Ala Cys Val Pro Arg Cys Pro Gln
                250                 255                 260

CCT CTT GTC TAC AAC AAG CTA ACT TTC CAG CTG GAA CCC AAT CCC CAC    930
Pro Leu Val Tyr Asn Lys Leu Thr Phe Gln Leu Glu Pro Asn Pro His
            265                 270                 275

ACC AAG TAT CAG TAT GGA GGA GTT TGT GTA GCC AGC TGT CCC CAT AAC    978
Thr Lys Tyr Gln Tyr Gly Gly Val Cys Val Ala Ser Cys Pro His Asn
        280                 285                 290

TTT GTG GTG GAT CAA ACA TCC TGT GTC AGG GCC TGT CCT CCT GAC AAG   1026
Phe Val Val Asp Gln Thr Ser Cys Val Arg Ala Cys Pro Pro Asp Lys
    295                 300                 305

ATG GAA GTA GAT AAA AAT GGG CTC AAG ATG TGT GAG CCT TGT GGG GGA   1074
Met Glu Val Asp Lys Asn Gly Leu Lys Met Cys Glu Pro Cys Gly Gly
310                 315                 320                 325

CTA TGT CCC AAA GCC TGT GAG GGA ACA GGC TCT GGG AGC CGC TTC CAG   1122
Leu Cys Pro Lys Ala Cys Glu Gly Thr Gly Ser Gly Ser Arg Phe Gln
                330                 335                 340

ACT GTG GAC TCG AGC AAC ATT GAT GGA TTT GTG AAC TGC ACC AAG ATC   1170
Thr Val Asp Ser Ser Asn Ile Asp Gly Phe Val Asn Cys Thr Lys Ile
            345                 350                 355

CTG GGC AAC CTG GAC TTT CTG ATC ACC GGC CTC AAT GGA GAC CCC TGG   1218
Leu Gly Asn Leu Asp Phe Leu Ile Thr Gly Leu Asn Gly Asp Pro Trp
        360                 365                 370

CAC AAG ATC CCT GCC CTG GAC CCA GAG AAG CTC AAT GTC TTC CGG ACA   1266
His Lys Ile Pro Ala Leu Asp Pro Glu Lys Leu Asn Val Phe Arg Thr
    375                 380                 385

GTA CGG GAG ATC ACA GGT TAC CTG AAC ATC CAG TCC TGG CCG CCC CAC   1314
Val Arg Glu Ile Thr Gly Tyr Leu Asn Ile Gln Ser Trp Pro Pro His
390                 395                 400                 405

ATG CAC AAC TTC AGT GTT TTT TCC AAT TTG ACA ACC ATT GGA GGC AGA   1362
Met His Asn Phe Ser Val Phe Ser Asn Leu Thr Thr Ile Gly Gly Arg
                410                 415                 420

AGC CTC TAC AAC CGG GGC TTC TCA TTG TTG ATC ATG AAG AAC TTG AAT   1410
Ser Leu Tyr Asn Arg Gly Phe Ser Leu Leu Ile Met Lys Asn Leu Asn
            425                 430                 435

GTC ACA TCT CTG GGC TTC CGA TCC CTG AAG GAA ATT AGT GCT GGG CGT   1458
Val Thr Ser Leu Gly Phe Arg Ser Leu Lys Glu Ile Ser Ala Gly Arg
        440                 445                 450

ATC TAT ATA AGT GCC AAT AGG CAG CTC TGC TAC CAC CAC TCT TTG AAC   1506
Ile Tyr Ile Ser Ala Asn Arg Gln Leu Cys Tyr His His Ser Leu Asn
    455                 460                 465
```

-continued

```
TGG ACC AAG GTG CTT CGG GGG CCT ACG GAA GAG CGA CTA GAC ATC AAG     1554
Trp Thr Lys Val Leu Arg Gly Pro Thr Glu Glu Arg Leu Asp Ile Lys
470                 475                 480                 485

CAT AAT CGG CCG CGC AGA GAC TGC GTG GCA GAG GGC AAA GTG TGT GAC     1602
His Asn Arg Pro Arg Arg Asp Cys Val Ala Glu Gly Lys Val Cys Asp
                490                 495                 500

CCA CTG TGC TCC TCT GGG GGA TGC TGG GGC CCA GGC CCT GGT CAG TGC     1650
Pro Leu Cys Ser Ser Gly Gly Cys Trp Gly Pro Gly Pro Gly Gln Cys
            505                 510                 515

TTG TCC TGT CGA AAT TAT AGC CGA GGA GGT GTC TGT GTG ACC CAC TGC     1698
Leu Ser Cys Arg Asn Tyr Ser Arg Gly Gly Val Cys Val Thr His Cys
        520                 525                 530

AAC TTT CTG AAT GGG GAG CCT CGA GAA TTT GCC CAT GAG GCC GAA TGC     1746
Asn Phe Leu Asn Gly Glu Pro Arg Glu Phe Ala His Glu Ala Glu Cys
    535                 540                 545

TTC TCC TGC CAC CCG GAA TGC CAA CCC ATG GAG GGC ACT GCC ACA TGC     1794
Phe Ser Cys His Pro Glu Cys Gln Pro Met Glu Gly Thr Ala Thr Cys
550                 555                 560                 565

AAT GGC TCG GGC TCT GAT ACT TGT GCT CAA TGT GCC CAT TTT CGA GAT     1842
Asn Gly Ser Gly Ser Asp Thr Cys Ala Gln Cys Ala His Phe Arg Asp
                570                 575                 580

GGG CCC CAC TGT GTG AGC AGC TGC CCC CAT GGA GTC CTA GGT GCC AAG     1890
Gly Pro His Cys Val Ser Ser Cys Pro His Gly Val Leu Gly Ala Lys
            585                 590                 595

GGC CCA ATC TAC AAG TAC CCA GAT GTT CAG AAT GAA TGT CGG CCC TGC     1938
Gly Pro Ile Tyr Lys Tyr Pro Asp Val Gln Asn Glu Cys Arg Pro Cys
        600                 605                 610

CAT GAG AAC TGC ACC CAG GGG TGT AAA GGA CCA GAG CTT CAA GAC TGT     1986
His Glu Asn Cys Thr Gln Gly Cys Lys Gly Pro Glu Leu Gln Asp Cys
    615                 620                 625

TTA GGA CAA ACA CTG GTG CTG ATC GGC AAA ACC CAT CTG ACA ATG GCT     2034
Leu Gly Gln Thr Leu Val Leu Ile Gly Lys Thr His Leu Thr Met Ala
630                 635                 640                 645

TTG ACA GTG ATA GCA GGA TTG GTA GTG ATT TTC ATG ATG CTG GGC GGC     2082
Leu Thr Val Ile Ala Gly Leu Val Val Ile Phe Met Met Leu Gly Gly
                650                 655                 660

ACT TTT CTC TAC TGG CGT GGG CGC CGG ATT CAG AAT AAA AGG GCT ATG     2130
Thr Phe Leu Tyr Trp Arg Gly Arg Arg Ile Gln Asn Lys Arg Ala Met
            665                 670                 675

AGG CGA TAC TTG GAA CGG GGT GAG AGC ATA GAG CCT CTG GAC CCC AGT     2178
Arg Arg Tyr Leu Glu Arg Gly Glu Ser Ile Glu Pro Leu Asp Pro Ser
        680                 685                 690

GAG AAG GCT AAC AAA GTC TTG GCC AGA ATC TTC AAA GAG ACA GAG CTA     2226
Glu Lys Ala Asn Lys Val Leu Ala Arg Ile Phe Lys Glu Thr Glu Leu
    695                 700                 705

AGG AAG CTT AAA GTG CTT GGC TCG GGT GTC TTT GGA ACT GTG CAC AAA     2274
Arg Lys Leu Lys Val Leu Gly Ser Gly Val Phe Gly Thr Val His Lys
710                 715                 720                 725

GGA GTG TGG ATC CCT GAG GGT GAA TCA ATC AAG ATT CCA GTC TGC ATT     2322
Gly Val Trp Ile Pro Glu Gly Glu Ser Ile Lys Ile Pro Val Cys Ile
                730                 735                 740

AAA GTC ATT GAG GAC AAG AGT GGA CGG CAG AGT TTT CAA GCT GTG ACA     2370
Lys Val Ile Glu Asp Lys Ser Gly Arg Gln Ser Phe Gln Ala Val Thr
            745                 750                 755

GAT CAT ATG CTG GCC ATT GGC AGC CTG GAC CAT GCC CAC ATT GTA AGG     2418
Asp His Met Leu Ala Ile Gly Ser Leu Asp His Ala His Ile Val Arg
        760                 765                 770

CTG CTG GGA CTA TGC CCA GGG TCA TCT CTG CAG CTT GTC ACT CAA TAT     2466
Leu Leu Gly Leu Cys Pro Gly Ser Ser Leu Gln Leu Val Thr Gln Tyr
    775                 780                 785
```

```
TTG CCT CTG GGT TCT CTG CTG GAT CAT GTG AGA CAA CAC CGG GGG GCA    2514
Leu Pro Leu Gly Ser Leu Leu Asp His Val Arg Gln His Arg Gly Ala
790             795                 800                 805

CTG GGG CCA CAG CTG CTG CTC AAC TGG GGA GTA CAA ATT GCC AAG GGA    2562
Leu Gly Pro Gln Leu Leu Leu Asn Trp Gly Val Gln Ile Ala Lys Gly
                810                 815                 820

ATG TAC TAC CTT GAG GAA CAT GGT ATG GTG CAT AGA AAC CTG GCT GCC    2610
Met Tyr Tyr Leu Glu Glu His Gly Met Val His Arg Asn Leu Ala Ala
        825                 830                 835

CGA AAC GTG CTA CTC AAG TCA CCC AGT CAG GTT CAG GTG GCA GAT TTT    2658
Arg Asn Val Leu Leu Lys Ser Pro Ser Gln Val Gln Val Ala Asp Phe
840                 845                 850

GGT GTG GCT GAC CTG CTG CCT CCT GAT GAT AAG CAG CTG CTA TAC AGT    2706
Gly Val Ala Asp Leu Leu Pro Pro Asp Asp Lys Gln Leu Leu Tyr Ser
855                 860                 865

GAG GCC AAG ACT CCA ATT AAG TGG ATG GCC CTT GAG AGT ATC CAC TTT    2754
Glu Ala Lys Thr Pro Ile Lys Trp Met Ala Leu Glu Ser Ile His Phe
870                 875                 880                 885

GGG AAA TAC ACA CAC CAG AGT GAT GTC TGG AGC TAT GGT GTG ACA GTT    2802
Gly Lys Tyr Thr His Gln Ser Asp Val Trp Ser Tyr Gly Val Thr Val
                890                 895                 900

TGG GAG TTG ATG ACC TTC GGG GCA GAG CCC TAT GCA GGG CTA CGA TTG    2850
Trp Glu Leu Met Thr Phe Gly Ala Glu Pro Tyr Ala Gly Leu Arg Leu
            905                 910                 915

GCT GAA GTA CCA GAC CTG CTA GAG AAG GGG GAG CGG TTG GCA CAG CCC    2898
Ala Glu Val Pro Asp Leu Leu Glu Lys Gly Glu Arg Leu Ala Gln Pro
        920                 925                 930

CAG ATC TGC ACA ATT GAT GTC TAC ATG GTG ATG GTC AAG TGT TGG ATG    2946
Gln Ile Cys Thr Ile Asp Val Tyr Met Val Met Val Lys Cys Trp Met
935                 940                 945

ATT GAT GAG AAC ATT CGC CCA ACC TTT AAA GAA CTA GCC AAT GAG TTC    2994
Ile Asp Glu Asn Ile Arg Pro Thr Phe Lys Glu Leu Ala Asn Glu Phe
950                 955                 960                 965

ACC AGG ATG GCC CGA GAC CCA CCA CGG TAT CTG GTC ATA AAG AGA GAG    3042
Thr Arg Met Ala Arg Asp Pro Pro Arg Tyr Leu Val Ile Lys Arg Glu
                970                 975                 980

AGT GGG CCT GGA ATA GCC CCT GGG CCA GAG CCC CAT GGT CTG ACA AAC    3090
Ser Gly Pro Gly Ile Ala Pro Gly Pro Glu Pro His Gly Leu Thr Asn
            985                 990                 995

AAG AAG CTA GAG GAA GTA GAG CTG GAG CCA GAA CTA GAC CTA GAC CTA    3138
Lys Lys Leu Glu Glu Val Glu Leu Glu Pro Glu Leu Asp Leu Asp Leu
        1000                1005                1010

GAC TTG GAA GCA GAG GAG GAC AAC CTG GCA ACC ACC ACA CTG GGC TCC    3186
Asp Leu Glu Ala Glu Glu Asp Asn Leu Ala Thr Thr Thr Leu Gly Ser
    1015                1020                1025

GCC CTC AGC CTA CCA GTT GGA ACA CTT AAT CGG CCA CGT GGG AGC CAG    3234
Ala Leu Ser Leu Pro Val Gly Thr Leu Asn Arg Pro Arg Gly Ser Gln
1030                1035                1040                1045

AGC CTT TTA AGT CCA TCA TCT GGA TAC ATG CCC ATG AAC CAG GGT AAT    3282
Ser Leu Leu Ser Pro Ser Ser Gly Tyr Met Pro Met Asn Gln Gly Asn
                1050                1055                1060

CTT GGG GAG TCT TGC CAG GAG TCT GCA GTT TCT GGG AGC AGT GAA CGG    3330
Leu Gly Glu Ser Cys Gln Glu Ser Ala Val Ser Gly Ser Ser Glu Arg
            1065                1070                1075

TGC CCC CGT CCA GTC TCT CTA CAC CCA ATG CCA CGG GGA TGC CTG GCA    3378
Cys Pro Arg Pro Val Ser Leu His Pro Met Pro Arg Gly Cys Leu Ala
        1080                1085                1090

TCA GAG TCA TCA GAG GGG CAT GTA ACA GGC TCT GAG GCT GAG CTC CAG    3426
Ser Glu Ser Ser Glu Gly His Val Thr Gly Ser Glu Ala Glu Leu Gln
1095                1100                1105
```

```
GAG AAA GTG TCA ATG TGT AGA AGC CGG AGC AGG AGC CGG AGC CCA CGG    3474
Glu Lys Val Ser Met Cys Arg Ser Arg Ser Arg Ser Arg Ser Pro Arg
1110            1115                1120                1125

CCA CGC GGA GAT AGC GCC TAC CAT TCC CAG CGC CAC AGT CTG CTG ACT    3522
Pro Arg Gly Asp Ser Ala Tyr His Ser Gln Arg His Ser Leu Leu Thr
        1130                1135                1140

CCT GTT ACC CCA CTC TCC CCA CCC GGG TTA GAG GAA GAG GAT GTC AAC    3570
Pro Val Thr Pro Leu Ser Pro Pro Gly Leu Glu Glu Glu Asp Val Asn
            1145                1150                1155

GGT TAT GTC ATG CCA GAT ACA CAC CTC AAA GGT ACT CCC TCC TCC CGG    3618
Gly Tyr Val Met Pro Asp Thr His Leu Lys Gly Thr Pro Ser Ser Arg
1160                1165                1170

GAA GGC ACC CTT TCT TCA GTG GGT CTT AGT TCT GTC CTG GGT ACT GAA    3666
Glu Gly Thr Leu Ser Ser Val Gly Leu Ser Ser Val Leu Gly Thr Glu
        1175                1180                1185

GAA GAA GAT GAA GAT GAG GAG TAT GAA TAC ATG AAC CGG AGG AGA AGG    3714
Glu Glu Asp Glu Asp Glu Glu Tyr Glu Tyr Met Asn Arg Arg Arg Arg
1190                1195                1200                1205

CAC AGT CCA CCT CAT CCC CCT AGG CCA AGT TCC CTT GAG GAG CTG GGT    3762
His Ser Pro Pro His Pro Pro Arg Pro Ser Ser Leu Glu Glu Leu Gly
            1210                1215                1220

TAT GAG TAC ATG GAT GTG GGG TCA GAC CTC AGT GCC TCT CTG GGC AGC    3810
Tyr Glu Tyr Met Asp Val Gly Ser Asp Leu Ser Ala Ser Leu Gly Ser
        1225                1230                1235

ACA CAG AGT TGC CCA CTC CAC CCT GTA CCC ATC ATG CCC ACT GCA GGC    3858
Thr Gln Ser Cys Pro Leu His Pro Val Pro Ile Met Pro Thr Ala Gly
1240                1245                1250

ACA ACT CCA GAT GAA GAC TAT GAA TAT ATG AAT CGG CAA CGA GAT GGA    3906
Thr Thr Pro Asp Glu Asp Tyr Glu Tyr Met Asn Arg Gln Arg Asp Gly
        1255                1260                1265

GGT GGT CCT GGG GGT GAT TAT GCA GCC ATG GGG GCC TGC CCA GCA TCT    3954
Gly Gly Pro Gly Gly Asp Tyr Ala Ala Met Gly Ala Cys Pro Ala Ser
1270                1275                1280                1285

GAG CAA GGG TAT GAA GAG ATG AGA GCT TTT CAG GGG CCT GGA CAT CAG    4002
Glu Gln Gly Tyr Glu Glu Met Arg Ala Phe Gln Gly Pro Gly His Gln
            1290                1295                1300

GCC CCC CAT GTC CAT TAT GCC CGC CTA AAA ACT CTA CGT AGC TTA GAG    4050
Ala Pro His Val His Tyr Ala Arg Leu Lys Thr Leu Arg Ser Leu Glu
        1305                1310                1315

GCT ACA GAC TCT GCC TTT GAT AAC CCT GAT TAC TGG CAT AGC AGG CTT    4098
Ala Thr Asp Ser Ala Phe Asp Asn Pro Asp Tyr Trp His Ser Arg Leu
1320                1325                1330

TTC CCC AAG GCT AAT GCC CAG AGA ACG TAACTCCTGC TCCCTGTGGC         4145
Phe Pro Lys Ala Asn Ala Gln Arg Thr
1335                1340

ACTCAGGGAG CATTTAATGG CAGCTAGTGC CTTTAGAGGG TACCGTCTTC TCCCTATTCC   4205

CTCTCTCTCC CAGGTCCCAG CCCCTTTTCC CCAGTCCCAG ACAATTCCAT CAATCTTTG    4265

GAGGCTTTTA AACATTTTGA CACAAAATTC TTATGGTATG TAGCCAGCTG TGCACTTTCT   4325

TCTCTTTCCC AACCCCAGGA AAGGTTTTCC TTATTTTGTG TGCTTTCCCA GTCCCATTCC   4385

TCAGCTTCTT CACAGGCACT CCTGGAGATA TGAAGGATTA CTCTCCATAT CCCTTCCTCT   4445

CAGGCTCTTG ACTACTTGGA ACTAGGCTCT TATGTGTGCC TTTGTTTCCC ATCAGACTGT   4505

CAAGAAGAGG AAAGGGAGGA AACCTAGCAG AGGAAAGTGT AATTTGGTT TATGACTCTT    4565

AACCCCCTAG AAAGACAGAA GCTTAAAATC TGTGAAGAAA GAGGTTAGGA GTAGATATTG   4625

ATTACTATCA TAATTCAGCA CTTAACTATG AGCCAGGCAT CATACTAAAC TTCACCTACA   4685

TTATCTCACT TAGTCCTTTA TCATCCTTAA AACAATTCTG TGACATACAT ATTATCTCAT   4745
```

-continued

```
TTTACACAAA GGGAAGTCGG GCATGGTGGC TCATGCCTGT AATCTCAGCA CTTTGGGAGG      4805

CTGAGGCAGA AGGATTACCT GAGGCAAGGA GTTTGAGACC AGCTTAGCCA ACATAGTAAG      4865

ACCCCCATCT CTTTAAAAAA AAAAAAAAAA AAAAAAAAA                             4905
```

(2) INFORMATION FOR SEQ ID NO:4:

(i) SEQUENCE CHARACTERISTICS:
      (A) LENGTH: 1342 amino acids
      (B) TYPE: amino acid
      (D) TOPOLOGY: linear (ii) MOLECULE TYPE: protein (xi) SEQUENCE DESCRIPTION: SEQ ID NO:4:

```
Met Arg Ala Asn Asp Ala Leu Gln Val Leu Gly Leu Leu Phe Ser Leu
 1               5                  10                  15

Ala Arg Gly Ser Glu Val Gly Asn Ser Gln Ala Val Cys Pro Gly Thr
             20                  25                  30

Leu Asn Gly Leu Ser Val Thr Gly Asp Ala Glu Asn Gln Tyr Gln Thr
         35                  40                  45

Leu Tyr Lys Leu Tyr Glu Arg Cys Glu Val Val Met Gly Asn Leu Glu
 50                  55                  60

Ile Val Leu Thr Gly His Asn Ala Asp Leu Ser Phe Leu Gln Trp Ile
 65                  70                  75                  80

Arg Glu Val Thr Gly Tyr Val Leu Val Ala Met Asn Glu Phe Ser Thr
             85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
            115                 120                 125

His Ala Leu Arg Gln Leu Arg Leu Thr Gln Leu Thr Glu Ile Leu Ser
        130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
    290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
                325                 330                 335
```

```
Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
            355                 360                 365

Asn Gly Asp Pro Trp His Lys Ile Pro Ala Leu Asp Pro Glu Lys Leu
            370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
                    405                 410                 415

Thr Ile Gly Gly Arg Ser Leu Tyr Asn Arg Gly Phe Ser Leu Leu Ile
            420                 425                 430

Met Lys Asn Leu Asn Val Thr Ser Leu Gly Phe Arg Ser Leu Lys Glu
            435                 440                 445

Ile Ser Ala Gly Arg Ile Tyr Ile Ser Ala Asn Arg Gln Leu Cys Tyr
            450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Arg Asp Cys Val Ala Glu
                    485                 490                 495

Gly Lys Val Cys Asp Pro Leu Cys Ser Ser Gly Cys Trp Gly Pro
            500                 505                 510

Gly Pro Gly Gln Cys Leu Ser Cys Arg Asn Tyr Ser Arg Gly Gly Val
            515                 520                 525

Cys Val Thr His Cys Asn Phe Leu Asn Gly Glu Pro Arg Glu Phe Ala
            530                 535                 540

His Glu Ala Glu Cys Phe Ser Cys His Pro Glu Cys Gln Pro Met Glu
545                 550                 555                 560

Gly Thr Ala Thr Cys Asn Gly Ser Gly Ser Asp Thr Cys Ala Gln Cys
                    565                 570                 575

Ala His Phe Arg Asp Gly Pro His Cys Val Ser Ser Cys Pro His Gly
                    580                 585                 590

Val Leu Gly Ala Lys Gly Pro Ile Tyr Lys Tyr Pro Asp Val Gln Asn
            595                 600                 605

Glu Cys Arg Pro Cys His Glu Asn Cys Thr Gln Gly Cys Lys Gly Pro
            610                 615                 620

Glu Leu Gln Asp Cys Leu Gly Gln Thr Leu Val Leu Ile Gly Lys Thr
625                 630                 635                 640

His Leu Thr Met Ala Leu Thr Val Ile Ala Gly Leu Val Val Ile Phe
                    645                 650                 655

Met Met Leu Gly Gly Thr Phe Leu Tyr Trp Arg Gly Arg Arg Ile Gln
            660                 665                 670

Asn Lys Arg Ala Met Arg Arg Tyr Leu Glu Arg Gly Glu Ser Ile Glu
            675                 680                 685

Pro Leu Asp Pro Ser Glu Lys Ala Asn Lys Val Leu Ala Arg Ile Phe
            690                 695                 700

Lys Glu Thr Glu Leu Arg Lys Leu Lys Val Leu Gly Ser Gly Val Phe
705                 710                 715                 720

Gly Thr Val His Lys Gly Val Trp Ile Pro Glu Gly Glu Ser Ile Lys
                    725                 730                 735

Ile Pro Val Cys Ile Lys Val Ile Glu Asp Lys Ser Gly Arg Gln Ser
            740                 745                 750

Phe Gln Ala Val Thr Asp His Met Leu Ala Ile Gly Ser Leu Asp His
```

-continued

```
                755                 760                 765
Ala His Ile Val Arg Leu Leu Gly Leu Cys Pro Gly Ser Ser Leu Gln
            770                 775                 780
Leu Val Thr Gln Tyr Leu Pro Leu Gly Ser Leu Leu Asp His Val Arg
785                 790                 795                 800
Gln His Arg Gly Ala Leu Gly Pro Gln Leu Leu Leu Asn Trp Gly Val
                805                 810                 815
Gln Ile Ala Lys Gly Met Tyr Tyr Leu Glu Glu His Gly Met Val His
            820                 825                 830
Arg Asn Leu Ala Ala Arg Asn Val Leu Leu Lys Ser Pro Ser Gln Val
            835                 840                 845
Gln Val Ala Asp Phe Gly Val Ala Asp Leu Leu Pro Pro Asp Asp Lys
850                 855                 860
Gln Leu Leu Tyr Ser Glu Ala Lys Thr Pro Ile Lys Trp Met Ala Leu
865                 870                 875                 880
Glu Ser Ile His Phe Gly Lys Tyr Thr His Gln Ser Asp Val Trp Ser
                885                 890                 895
Tyr Gly Val Thr Val Trp Glu Leu Met Thr Phe Gly Ala Glu Pro Tyr
            900                 905                 910
Ala Gly Leu Arg Leu Ala Glu Val Pro Asp Leu Leu Glu Lys Gly Glu
            915                 920                 925
Arg Leu Ala Gln Pro Gln Ile Cys Thr Ile Asp Val Tyr Met Val Met
930                 935                 940
Val Lys Cys Trp Met Ile Asp Glu Asn Ile Arg Pro Thr Phe Lys Glu
945                 950                 955                 960
Leu Ala Asn Glu Phe Thr Arg Met Ala Arg Asp Pro Pro Arg Tyr Leu
                965                 970                 975
Val Ile Lys Arg Glu Ser Gly Pro Gly Ile Ala Pro Gly Pro Glu Pro
            980                 985                 990
His Gly Leu Thr Asn Lys Lys Leu Glu Glu Val Glu Leu Glu Pro Glu
            995                 1000                1005
Leu Asp Leu Asp Leu Asp Leu Glu Ala Glu Glu Asp Asn Leu Ala Thr
            1010                1015                1020
Thr Thr Leu Gly Ser Ala Leu Ser Leu Pro Val Gly Thr Leu Asn Arg
1025                1030                1035                1040
Pro Arg Gly Ser Gln Ser Leu Leu Ser Pro Ser Ser Gly Tyr Met Pro
                1045                1050                1055
Met Asn Gln Gly Asn Leu Gly Glu Ser Cys Gln Glu Ser Ala Val Ser
                1060                1065                1070
Gly Ser Ser Glu Arg Cys Pro Arg Pro Val Ser Leu His Pro Met Pro
            1075                1080                1085
Arg Gly Cys Leu Ala Ser Glu Ser Ser Glu Gly His Val Thr Gly Ser
            1090                1095                1100
Glu Ala Glu Leu Gln Glu Lys Val Ser Met Cys Arg Ser Arg Ser Arg
1105                1110                1115                1120
Ser Arg Ser Pro Arg Pro Arg Gly Asp Ser Ala Tyr His Ser Gln Arg
                1125                1130                1135
His Ser Leu Leu Thr Pro Val Thr Pro Leu Ser Pro Pro Gly Leu Glu
            1140                1145                1150
Glu Glu Asp Val Asn Gly Tyr Val Met Pro Asp Thr His Leu Lys Gly
            1155                1160                1165
Thr Pro Ser Ser Arg Glu Gly Thr Leu Ser Ser Val Gly Leu Ser Ser
            1170                1175                1180
```

-continued

```
Val Leu Gly Thr Glu Glu Asp Glu Asp Glu Tyr Glu Tyr Met
1185                1190                1195                1200

Asn Arg Arg Arg Arg His Ser Pro Pro His Pro Arg Pro Ser Ser
        1205                1210                1215

Leu Glu Glu Leu Gly Tyr Glu Tyr Met Asp Val Gly Ser Asp Leu Ser
            1220                1225                1230

Ala Ser Leu Gly Ser Thr Gln Ser Cys Pro Leu His Pro Val Pro Ile
        1235                1240                1245

Met Pro Thr Ala Gly Thr Thr Pro Asp Glu Asp Tyr Glu Tyr Met Asn
        1250                1255                1260

Arg Gln Arg Asp Gly Gly Pro Gly Gly Asp Tyr Ala Ala Met Gly
1265                1270                1275                1280

Ala Cys Pro Ala Ser Glu Gln Gly Tyr Glu Glu Met Arg Ala Phe Gln
            1285                1290                1295

Gly Pro Gly His Gln Ala Pro His Val His Tyr Ala Arg Leu Lys Thr
            1300                1305                1310

Leu Arg Ser Leu Glu Ala Thr Asp Ser Ala Phe Asp Asn Pro Asp Tyr
            1315                1320                1325

Trp His Ser Arg Leu Phe Pro Lys Ala Asn Ala Gln Arg Thr
            1330                1335                1340
```

(2) INFORMATION FOR SEQ ID NO:5:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:5:

```
Glu Asp Glu Asp Glu Glu Tyr Glu Tyr Met Asn Arg Arg Arg Arg
1               5                   10                  15
```

(2) INFORMATION FOR SEQ ID NO:6:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:6:

```
Thr Thr Pro Asp Glu Asp Tyr Glu Tyr Met Asn Arg Gln Arg Asp
1               5                   10                  15
```

(2) INFORMATION FOR SEQ ID NO:7:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:7:

```
Thr Glu Glu Arg Leu Asp Ile Lys His Asn Arg Pro Arg Arg Asp
1               5                   10                  15
```

(2) INFORMATION FOR SEQ ID NO:8:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:8:

```
Arg Ser Arg Ser Arg Ser Arg Ser Pro Arg Pro Arg Gly Asp Ser
1               5                   10                  15
```

(2) INFORMATION FOR SEQ ID NO:9:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:9:

```
Tyr Met Asn Arg Arg Arg Arg His Ser Pro Pro His Pro Pro Arg
1               5                   10                  15
```

(2) INFORMATION FOR SEQ ID NO:10:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GATCTCGAGT CGAC                                14

(2) INFORMATION FOR SEQ ID NO:11:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GATCGTCGAC TCGA                                14

(2) INFORMATION FOR SEQ ID NO:12:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:12:

Tyr Glu Tyr Met Asn
1               5

What is claimed is:

1. A method for screening a ligand of an erbB-3 receptor protein, identified as having the amino acid sequence SEQ ID NO:4 or as the mature gp180$^{erbB}$-3 protein, for the ability to bind the extracellular domain of the erbB-3 receptor comprising:
   a) contacting the ligand with the extracellular domain of the erbB-3 receptor protein under conditions whereby the ligand can bind the extracellular domain of the erbB-3 receptor protein; and
   b) detecting binding of the ligand to the extracellular domain of the erbB-3 receptor protein.

2. The method of claim 1, wherein the extracellular domain of the erbB-3 receptor protein is on the surface of a cell expressing the erbB-3 receptor protein.

3. A method for screening a ligand of an erbB-3 receptor protein, identified as having the amino acid sequence SEQ ID NO:4 or as the mature gp180$^{erbB-3}$ protein, for the ability to affect an activity mediated by the erbB-3 receptor protein, comprising:
   a) contacting a ligand with an erbB-3 receptor protein under conditions whereby the ligand can bind the extracellular domain of the erbB-3 receptor protein; and
   b) detecting a biological activity mediated by the binding of the ligand to the erbB-3 receptor protein.

4. The method of claim 3, wherein the detecting step comprises measuring the level of erbB-3 receptor protein-mediated intrinsic tyrosine phosphorylation.

5. The method of claim 3, wherein the detecting step comprises measuring the level of cell growth in cells expressing the erbB-3 receptor protein to which the ligand is bound.

6. The method of claim 3, wherein the detecting step comprises measuring the level of DNA synthesis in cells expressing the erbB-3 receptor protein to which the ligand is bound.

7. The method of claim 3, wherein the detecting step comprises measuring the level of synthesis of erbB-3 receptor protein encoding mRNA in cells expressing the erbB-3 receptor protein to which the ligand is bound.

8. A method for detecting the presence of an activating ligand of an erbB-3 receptor protein, identified as having the amino acid sequence SEQ ID NO:4 or as the mature gp180$^{erbB-3}$ protein, in a biological source, comprising:
   a) contacting the biological source with cells from a cell line that expresses an erbB-3 receptor protein under conditions whereby an activating ligand in the biological source can bind the erbB-3 receptor protein;
   b) detecting the amount of erbB-3 receptor protein activation in the cells of step (a);
   c) detecting the amount of erbB-3 receptor protein activation in cells from the cell line that expresses an erbB-3 receptor protein which are not contacted with the biological source; and
   d) comparing the amount of erbB-3 receptor protein activation in the cells of step (b) with the amount of erbB-3 receptor protein activation in the cells of step (c), whereby a greater amount of erbB-3 receptor protein activation in the cells of step (b) indicates the presence of an activating ligand of an erbB-3 receptor protein in the biological source.

9. The method of claim 8, wherein the detecting step comprises detecting the level of erbB-3 receptor protein-mediated intrinsic tyrosine phosphorylation.

10. The method of claim 8, wherein the detecting step comprises detecting the level of cell growth.

11. The method of claim 8, wherein the detecting step comprises detecting the level of DNA synthesis.

12. The method of claim 8, wherein the detecting step comprises measuring the level of erbB-3 receptor protein mRNA synthesis.

13. The method of claim 8, wherein the erbB-3 receptor protein is overexpressed by the cell line.

14. The method of claim 8, further comprising the step of purifying the activating ligand of the erbB-3 receptor protein.

15. A method for detecting the presence of a blocking ligand of an erbB-3 receptor protein, identified as having the amino acid sequence SEQ ID NO:4 or as the mature gp180$^{erbB-3}$ protein, in a biological source, comprising:
   a) contacting the biological source with cells from a cell line that expresses erbB-3 receptor protein under conditions whereby a blocking ligand in the biological source can bind the erbB-3 receptor protein;
   b) detecting the amount of erbB-3 receptor protein activation in the cells of step (a);
   c) detecting the amount of erbB-3 receptor protein activation in cells from the cell line that expresses an erbB-3 receptor protein which are not contacted with the biological source; and
   d) comparing the amount of erbB-3 receptor protein activation in the cells of step (b) with the amount of erbB-3 receptor protein activation in the cells of step (c), whereby a greater amount of erbB-3 receptor protein activation in the cells of step (c) indicates the presence of a blocking ligand of an erbB-3 receptor protein in the biological source.

16. The method of claim 15, wherein the detecting step comprises detecting the level of erbB-3 receptor protein-mediated intrinsic tyrosine phosphorylation.

17. The method of claim 15, wherein the detecting step comprises detecting the level of cell growth.

18. The method of claim 15, wherein the detecting step comprises detecting the level of DNA synthesis.

19. The method of claim 15, wherein the detecting step comprises measuring the level of erbB-3 receptor protein MRNA synthesis.

20. The method of claim 15, wherein the erbB-3 receptor protein is overexpressed by the cell line.

21. The method of claim 15, further comprising the step of purifying the blocking ligand of the erbB-3 receptor protein.

22. A method of decreasing a biochemical or biological activity mediated by an erbB-3 receptor protein, identified as having the amino acid sequence SEQ ID NO:4 or as the mature gp180$^{erbB-3}$ protein, comprising blocking the binding of an erbB-3 activating ligand to the extracellular domain of the erbB-3 receptor protein.

23. The method of claim 22, wherein the blocking is accomplished by an antibody reactive with the ligand binding domain of the erbB-3 receptor protein.

24. The method of claim 22, wherein the blocking is accomplished by a blocking ligand of the erbB-3 receptor protein.

25. A method of promoting a biochemical or biological activity mediated by an erbB-3 receptor protein, identified as having the amino acid sequence SEQ ID NO:4 or as the mature gp180$^{erbB-3}$ protein, comprising contacting an activating ligand of the erbB-3 receptor protein with the extracellular domain of the erbB-3 receptor protein under conditions whereby the activating ligand can bind the extracellular domain of the erbB-3 receptor protein.

26. A method for detecting the presence of an erbB-3 receptor protein antigen in a biological sample comprising the steps of:
  a) contacting the sample with an antibody specific for the erbB-3 receptor protein, identified as having the amino acid sequence SEQ ID NO:4 or as the mature gp180$^{erbB-3}$ protein, or a portion of SEQ ID NO:4 sufficient to provide an erbB-3 receptor binding site for an antibody thereto which antibody is further characterized by not binding erbB-2 or erbB, under conditions whereby an antigen/antibody complex can form; and
  b) detecting the formation an antigen/antibody complex, whereby the formation of an antigen/antibody complex indicates the presence of an erbB-3 receptor protein antigen in the biological sample.

27. The method of claim 22, wherein the antibody is specific for the amino acid sequence selected from the group consisting of SEQ ID NO:5, SEQ ID NO:6, SEQ ID NO:7, SEQ ID NO:8 and SEQ ID NO:9.

28. A method of detecting the overexpression of an erbB-3 receptor protein, identified as having the amino acid sequence SEQ ID NO:4 or as the mature gp180$^{erbB-3}$ protein, in a biological sample from a subject, comprising detecting the amount of erbB-3 receptor protein in the biological sample from the subject and comparing the amount of erbB-3 receptor protein in the biological sample from the subject to an amount of erbB-3 receptor protein in an equivalent biological sample known to have normal erbB-3 receptor protein expression, whereby an amount of erbB-3 receptor protein in the biological sample from the subject greater than the amount of erbB-3 receptor protein in the equivalent biological sample known to have normal erbB-3 receptor protein expression indicates overexpression of the erbB-3 receptor protein in the biological sample from the subject.

29. The method of claim 28, further comprising correlating the overexpression of the erbB-3 receptor protein with the presence of a neoplastic condition in the subject.

30. A method of detecting the activation of an erbB-3 receptor protein, identified as having the amino acid sequence SEQ ID NO:4 or as the mature gp180$^3$ protein, in a biological sample from a subject, comprising detecting phosphorylation of the erbB-3 receptor protein, whereby phosphorylation of the erbB-3 receptor protein in the biological sample indicates activation of the erbB-3 receptor protein in the biological sample from the subject.

31. The method of claim 30, further comprising:
  a) comparing the amount of erbB-3 receptor protein phosphorylation in biological sample from the subject to an amount of erbB-3 receptor protein phosphorylation in a biological sample from a second subject known to have normal erbB-3 receptor protein phosphorylation; and
  b) correlating an amount of phosphorylation in the biological sample from the subject greater than the amount of erbB-3 receptor protein phosphorylation in the biological sample from the second subject known to have normal erbB-3 receptor protein phosphorylation with the presence of a neoplastic condition in the subject.

* * * * *